(12) United States Patent
Liotta et al.

(10) Patent No.: US 6,399,783 B1
(45) Date of Patent: Jun. 4, 2002

(54) METHODS FOR THE ESTERIFICATION OF ALCOHOLS AND COMPOUNDS USEFUL THEREFOR AS POTENTIAL ANTICANCER AGENTS

(75) Inventors: Dennis C. Liotta, McDonough; Hariharan Venkatesan, Atlanta, both of GA (US); Laura Captain, Durham, NC (US); Michael V. Voronkov, Gainseville, FL (US); James P. Snyder; Marcus A. Schestopol, both of Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/645,766

(22) Filed: Aug. 25, 2000

Related U.S. Application Data

(62) Division of application No. 08/989,590, filed on Dec. 12, 1997, now Pat. No. 6,150,537.

(51) Int. Cl.$^7$ .................... C07D 233/04; C07D 263/08; C07D 277/08

(52) U.S. Cl. .................... 548/110; 548/188; 548/194; 548/230; 548/233; 548/322.5; 548/332.1

(58) Field of Search ................ 548/110, 188, 548/194, 230, 233, 322.5, 332.1

(56) References Cited

U.S. PATENT DOCUMENTS

| | | | |
|---|---|---|---|
| 5,136,060 A | * 8/1992 | Holton | 549/510 |
| 5,254,703 A | * 10/1993 | Holton | 549/510 |
| 5,300,638 A | * 4/1994 | Farina et al. | 540/357 |
| 5,352,806 A | * 10/1994 | Gunawardana et al. | 549/510 |
| 5,384,399 A | * 1/1995 | Holton | 544/97 |
| 5,405,972 A | * 4/1995 | Holton et al. | 549/214 |
| 5,440,057 A | * 8/1995 | Nicolaou et al. | 549/511 |
| 5,461,162 A | * 10/1995 | Ho et al. | 548/188 |
| 5,461,169 A | * 10/1995 | Nicolaou et al. | 549/510 |
| 5,532,363 A | * 7/1996 | Holton | 544/97 |
| 5,597,931 A | * 1/1997 | Danishefsky et al. | 549/214 |
| 5,599,942 A | * 2/1997 | Bouchard et al. | 548/215 |
| 5,675,025 A | * 10/1997 | Sisti et al. | 549/510 |
| 5,773,629 A | * 6/1998 | Yang et al. | 548/239 |

FOREIGN PATENT DOCUMENTS

| | | |
|---|---|---|
| EP | 0561614 A2 * | 9/1993 |
| FR | 2 696 464 * | 4/1994 |
| JP | 80145650 * | 11/1980 |
| WO | WO 94/10169 * | 5/1994 |
| WO | WO 94/18186 * | 8/1994 |
| WO | WO 94/29288 * | 12/1994 |
| WO | WO 97/00870 * | 1/1997 |
| WO | WO 97/15562 * | 5/1997 |

OTHER PUBLICATIONS

Kanazawa et al., Direct, Stereoselective Synthesis of the Protected Paclitaxel (Taxol) Side Chain and High–yield Transformation to Paclitaxel, J. Chem. Soc., Chem. Commun., pp. 2591–2592, 1994.*

Nagao et al., Monitored Aminolysis of 3–Acyl–1, 3–thiazolidine–2–thiones: Synthesis of Amides and Amide Alkaloids, Chem. Pharm. Bull. vol. 32, pp. 2687–2694, 1984.*

Nagao et al., A New Practical Synthesis Method: Monitored Aminolysis of 3–Acyl–1,3–Thiazolidine–2–Thione, Heterocycles, vol. 17, pp. 537–554, 1982.

(List continued on next page.)

Primary Examiner—Brenda Coleman
(74) Attorney, Agent, or Firm—Needle & Rosenberg, P.C.

(57) ABSTRACT

The invention relates to a method for preparing an ester, by admixing a compound having the structure I or IV:

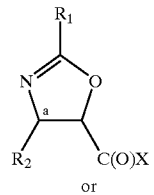

(I)

or

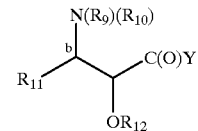

(IV)

with a base and an alcohol to produce an ester, wherein the alcohol is a precursor to Taxol and its analogs. The present invention also relates to compounds having the structure I and IV and methods of main them therefor. The invention also relates to the esterification of an alcohol by adding an alkoxide to a compound having the structure, VII:

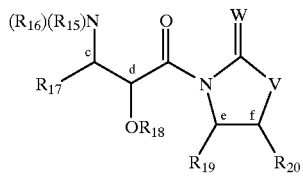

(VII)

The invention further relates to compounds having the structure I, IV, and VII and methods of making them therefor. The invention further relates to alcohols, and in particular, alcohols that are synthetic precursors to Taxol and analogs thereof.

16 Claims, No Drawings

OTHER PUBLICATIONS

Fujita et al., Chiral Induction Using Heterocycles, Advances In Heterocyclic Chemistry, vol. 45, pp. 1–37, 1989.

Hsiao et al., The Use if Cysteine– and Serine–Derived Thiazolidinethiones and Oxazoldinethiones as Efficient Chiral Auxiliaries in Aldol Condensations, J. Org. Chem., 52, pp. 2201–2206, 1987.

Evans et al., Enantioselective Aldol Condensations, 2, Erythro–Selective Chiral Aldol Condensation via Boron Enolates, J. Am. Soc., vol. 103, pp. 2127–2129, 1981.

Ghosh et al., Highly Enantioselective Aldol Reaction: Development of a New Chiral Auiliary from cis–1–Amino–2–hydroxyindan, J. Chem. Soc. Chem. Commun., pp. 1673–1674, 1992.

Evans et al., Stereoselective Aldol Condensation via Boron Enolates, J. Am. Chem. Soc., vol. 103, No. 11, pp. 3099–3111, 1981.

Oppolzer et al., Bornanesultam–Directed Asymmetric Synthesis of Crystalline, Enantiomerically Pure Syn Adols, J. Am. Chem. Soc., vol. 112, pp. 2767–2772, 1990.

Bunnage et al., Asymmetric Synthesis of the Taxol and Taxotere C–13 Side Chains, J. Chem. Soc. Perkin Trans., pp. 2385–2391, 1994.

Wang et al., Large–Scale and Highly Enantioselective Synthesis of the Taxol C–13 Side Chain through Asymmetric Dihydroxylation, J. Org. Chem, vol. 59, pp. 5104–5105, 1994.

Ojima et al., New and Efficient Approaches to the Semisynthesis of Taxol and Its C–13 Side Chain Analogs by Means of β–Lactm Synthon Method, Tetrahedron, vol. 48, No. 34, pp. 6985–7012, 1992.

Cabri, A High Yield Semisynthetic Apporach to 2'–epi–Taxol, Tetrahedron Letters, vol. 37, No. 27, pp. 4785–4786, 1996.

Kingston et al., Synthesis of Taxol from Baccatin III via an Oxazoline Intermediate, Tetrahedron Letters, vol. 35, No. 26, pp. 4483–4484, 1994.

Commercon et al., Improved Protection and Esterification of a Precursor of the Taxotere® and Taxol Side Chains, Tetrahedron Letters, vol. 33, No. 36, pp. 5185–5188, 1992.

Gennari et al., Taxol Semisynthesis: A Highly Enantio– and Diastereoselective Synthesis of the Side Chain and a New Method for Ester Formation at C–13 Using Thioesters, J. Org. Chem, vol. 62, No. 14, pp. 4746–4755, 1997.

Legters et al., "Synthesis of β–amino–a–hydroxy carboxylic acid esters from oxiranecarboxylic esters," Recveil Des Travaux, Chimiques Des Pays–Bas. vol. 11, pp. 69–74, Feb. 2, 1992.

Nagao et al. "Highly Diastereoselective Alkylation of Chiral Tin (II) Enolates onto Cyclic Acyl Imines. An Efficient Asymmetric Synthesis of Bicyclic Alkaloids Bearing a Nitrogen Atom Ring Juncture," J. Org. Chem. 55, pp. 1148–1156, 1990.

* cited by examiner

METHODS FOR THE ESTERIFICATION OF ALCOHOLS AND COMPOUNDS USEFUL THEREFOR AS POTENTIAL ANTICANCER AGENTS

This application is a divisional of, and claims the benefit of, application Ser. No. 08/989,590, filed Dec. 12, 1997, U.S. Pat. No. 6,150,537, which application is hereby incorporated herein by this reference.

ACKNOWLEDGEMENTS

This invention was made with government support under grants AI28731-07 and AI31827-05 awarded by the National Institutes of Health. The government has certain rights in the invention.

FIELD OF THE INVENTION

The invention relates to methods for esterifying alcohols. In particular, the invention provides novel compounds and methods useful in the production of Taxol and Taxol analogs.

BACKGROUND OF THE INVENTION

The esterification of alcohols is a common reaction in organic synthesis. Once the ester is produced, the ester can undergo further reactions to produce complex molecules. This approach is especially significant in the synthesis of natural products and non-natural synthetic compounds that exhibit biological activity. By converting a hydroxyl group to an ester, the chemical properties of the compound can change dramatically. An example of this improved property is the anti-cancer drug, Taxol.

Taxol and other antitumor taxoids constitute some of the most important discoveries in cancer chemotherapy in recent years. Taxol and Taxotere, which is a semi-synthetic analog of Taxol, have been approved by the FDA for the treatment of advanced ovarian and breast cancer. Additionally Taxol and Taxotere may be useful for the treatment of non-small-cell lung cancer, head and neck cancer and several other cancers. The structures of Taxol and Taxotere are shown below.

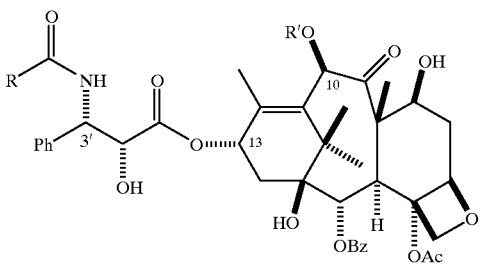

Taxol: R = Ph; R' = Ac
Taxotere: R = t-BuO; R' = H

Taxol and Taxotere differ in their structure at the C-10 and C-3' positions. While Taxol was first isolated from the bark of the pacific yew tree, *Taxus brevifola*, Taxotere, a synthetic analog of Taxol, possesses better bioavailability than Taxol. Due to the limited availability of Taxol from the yew tree (1 Kg from 10000 Kg of bark), different strategies including total synthesis, semisynthesis, cell and tissue culture of taxus spp., have been investigated so that large amounts of Taxol can be produced. Although the total synthesis of Taxol was accomplished in 1994, lengthy multi-step sequences led to poor overall yield of Taxol. Therefore, total synthesis has not to date been a viable alternative to solve the supply problem.

One approach to a large scale production of Taxol and Taxotere is their semisynthesis from 10-deacetyl baccatin III (referred to as baccatin III or baccatin), shown below. Baccatin III can be readily obtained from the needles of the yew tree *Taxus baccata*. Importantly, yew needles can be quickly regenerated; therefore, a continuous supply of Taxol may be available without affecting the yew population.

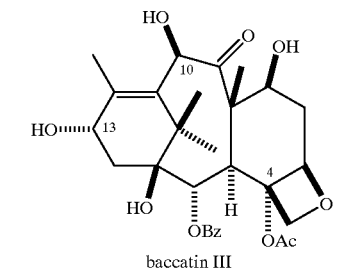

baccatin III

Structure-activity relationships of Taxol derivatives indicate that the C-13 N-benzoyl-3-phenyl isoserine side chain, with the 2'R, 3'S stereochemistry, is of crucial importance for Taxol's cytotoxicity. Although there are methods in the art for the asymmetric synthesis of the C-13 side chain, coupling the side chain to the C-13 hydroxyl group is not a simple endeavor. The coupling reaction is complicated by the fact that the C-13 hydroxyl group is situated in the skeletal concavity of baccatin III, which makes this hydroxyl group sterically hindered. Furthermore, the C-13 hydroxyl group has been proposed to form a stabilizing hydrogen bond with the C-4 acetate moiety. These two factors contribute to the difficulty encountered in attaching the side chain to the C-13 hydroxyl group.

One approach to attaching the isoserine side chain to the C-13-hydroxyl group involves a condensation reaction between baccatin and an isoserine acid. Greene et al. (*J. Am. Chem. Soc.* 1988, 110, 5917) discloses the direct esterification reaction of a protected form of baccatin III and an isoserine acid under vigorous conditions (73° C. for 4 days). International Patent Application No. WO 94/18186 to Swindell et al.; U.S. Pat. No. 5,675,025 to Sisti et al.; and U.S. Pat. No. 5,597,931 to Danishefsky et al. also disclose the condensation reaction between protected baccatins and isoserine acids and esters.

Another approach involves the condensation reaction between a heterocycle containing a carboxylic acid group and baccatin, followed by treatment with an acid to open the ring and produce the side chain at C-13. Kingston et al. (*Tetrahedron Letters* 1994, vol 35, no. 26, pp 4483) and International Patent Application No. WO 97/00870 to Gennari et al. disclose the coupling of oxazolidines and baccatin via a condensation reaction. U.S. Pat. No. 5,599,942 to Bouchard et al.; International Patent Application No. WO 94/10169 to Denis et al.; International Patent Application No. WO 94/10169; and Kanazawa et al. (*J. Chem. Chem. Com.* 1994, 2591) disclose the coupling of a 1,3-oxazole with baccatin followed by acid hydrolysis produced Taxol and derivatives thereof. In the respective condensation reactions disclosed in the above-identified patents and articles, the stereochemistry at C-2 of the heterocycle, wherein C-2 is the carbon bonded to the carboxylic acid group, has to be established (either S or R stereochemistry).

Gennari et al. (*Angew. Chem. Int. Ed. Engl.* 1996, 35, 1723) discloses the reaction between a protected baccatin and a thioester of an oxazolidine in the presence of a base. In the case of the oxazolidine, seven steps were required to produce the oxazolidine with the thioester group, wherein the first step involves the use of chiral boron agent. The resulting oxazolidine thioester produced and subsequently coupled with baccatin is the anti isomer and not the syn isomer. The coupling reaction involves adding a base to a mixture of the protected baccatin and the oxazolidine thioester. An excess of oxazolidine thioester (3.5 equivalents) and base (4.5 equivalents) are used in the coupling reaction. Similar to the condensation reactions described above, the stereochemistry at C-2 of the oxazolidine thioester is also established.

Therefore, there remains a need for a more efficient, high yield synthesis of Taxol and other similar compounds. In addition, there exists a need for synthetic methods where the stereochemistry at C2 of the precursor to the side chain does not have to be established.

SUMMARY OF THE INVENTION

To overcome the shortcomings described above, the present invention, in one aspect, relates to a method for preparing an ester, comprising:

(a) admixing a compound having the structure I:

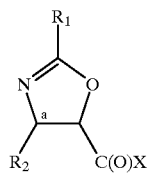

I wherein,
$R_1$ and $R_2$ are, independently, from $C_1$ to $C_{12}$ branched or straight chain alkyl; or substituted or unsubstituted aryl; and
X is a halogen or $OR_3$, wherein $R_3$, is from $C_1$ to $C_{12}$ branched or straight chain alkyl; substituted or unsubstituted aryl; aralkyl; acyl; or $S(O)_2R_{41}$, wherein $R_{41}$ is $C_1$ to $C_{12}$ branched or straight chain alkyl; or substituted or unsubstituted aryl, with a base to form an intermediate; and (b) admixing the intermediate of step (a) with an alcohol, an alkoxide, or a combination thereof.

The invention further relates to a method for preparing an ester, comprising admixing a compound having the structure III:

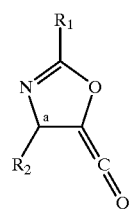

III wherein,
$R_1$ and $R_2$ are, independently, from $C_1$ to $C_{12}$ branched or straight chain alkyl or substituted or unsubstituted aryl,
with an alcohol, an alkoxide or a combination thereof.

The invention further relates to a method for preparing an ester, comprising admixing:

(a) a base;
(b) an alcohol, an alkoxide or a combination thereof; and
(c) a compound having the structure I:

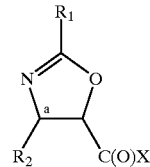

I wherein,
$R_1$ and $R_2$ are, independently, from $C_1$ to $C_{12}$ branched or straight chain alkyl; or substituted or unsubstituted aryl; and
X is a halogen or $OR_3$, wherein $R_3$ is from $C_1$ to $C_{12}$ branched or straight chain alkyl; substituted or unsubstituted aryl; aralkyl; acyl, $S(O)_2R_{41}$, wherein $R_{41}$ is $C_1$ to $C_{12}$ branched or straight chain alkyl; or substituted or unsubstituted aryl.

The invention further relates to a method for preparing an ester, comprising admixing:

(a) a base;
(b) an alcohol, an alkoxide or a combination thereof; and
(c) a compound having the structure IV:

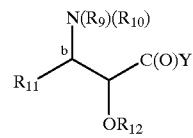

IV wherein,
$R_9$ and $R_{10}$ are, independently, an aralkyl or $C(O)R_{31}$, wherein $R_{31}$ is $C_1$ to $C_{12}$ straight chain or branched alkyl; substituted or unsubstituted aryl; or aralkyl;
$R_{11}$ is from $C_1$ to $C_{12}$ branched or straight chain alkyl or substituted or unsubstituted aryl;
$R_{12}$ is silyl, alkyl, acyl, aryl, or aralkyl; and
Y is a halogen or $OR_{13}$, wherein $R_{13}$ is from $C_1$ to $C_{12}$ branched or straight chain alkyl; or substituted or unsubstituted aryl; aralkyl; acyl; or $S(O)_2R_{42}$, wherein $R_{42}$ is $C_1$ to $C_{12}$ straight chain or branched alkyl; or substituted or unsubstituted aryl.

The invention further relates to a method for preparing an ester, comprising admixing:

(a) an alcohol, an alkoxide, or a combination thereof; and
(b) a compound having the structure V:

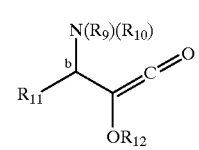

V wherein,
$R_9$ and $R_{10}$ are, independently, an aralkyl or $C(O)R_{31}$, wherein $R_{31}$ is $C_1$ to $C_{12}$ straight chain or branched alkyl; substituted or unsubstituted aryl; or aralkyl;

$R_{11}$ is from $C_1$ to $C_{12}$ branched or straight chain alkyl or substituted or unsubstituted aryl; and $R_{12}$ is silyl, alkyl, aryl, aralkyl or acyl.

The invention further relates to a method for preparing a compound having the structure I:

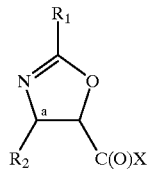

I wherein, $R_1$ and $R_2$ are, independently, from $C_1$ to $C_{12}$ branched or straight chain alkyl or substituted or unsubstituted aryl; and X is $OR_3$, wherein $R_3$ is from $C_1$ to $C_{12}$ branched or straight chain alkyl; substituted or unsubstituted aryl; aralkyl; acyl, or $S(O)_2R_{41}$, wherein $R_{41}$ is $C_1$ to $C_{12}$ branched or straight chain alkyl; or substituted or unsubstituted aryl, and $R_2$ and C(O)X are cis to one another, comprising:

(a) admixing a compound having the structure VI:

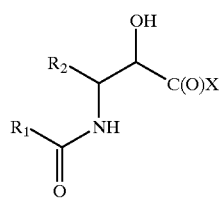

VI wherein, $R_1$ and $R_2$ are, independently, from $C_1$ to $C_{12}$ branched or straight chain alkyl or substituted or unsubstituted aryl;

X is $OR_3$, wherein $R_3$ is from $C_1$ to $C_{12}$ branched or straight chain alkyl; substituted or unsubstituted aryl; aralkyl; acyl, or $S(O)_2R_{41}$, wherein $R_{41}$ is $C_1$ to $C_{12}$ branched or straight chain alkyl; or substituted or unsubstituted aryl; and the hydroxyl group and amide group are cis to one another, with a cyclization agent.

The invention further relates to a compound having the formula I:

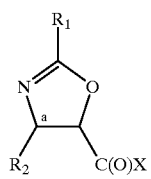

I wherein, $R_1$ and $R_2$ are, independently, from $C_1$ to $C_{12}$ branched or straight chain alkyl or substituted or unsubstituted aryl;

X is $OR_3$, wherein $R_3$ is halogen; $C_1$ to $C_{12}$ branched or straight chain alkyl; substituted or unsubstituted aryl;

aralkyl; acyl, aralkyl, or $S(O)_2R_{41}$, wherein $R_{41}$ is $C_1$ to $C_{12}$ branched or straight chain alkyl; or substituted or unsubstituted aryl; and $R_2$ and C(O)X are cis to one another.

The invention further relates to a compound having the structure IV:

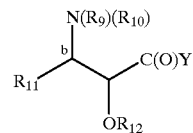

IV wherein, $R_9$ and $R_{10}$ are aralkyl;

$R_{11}$ is substituted or unsubstituted aryl;

$R_{12}$ is acyl, silyl, alkyl, aryl or aralkyl; and

Y is a halogen or $OR_{13}$, wherein $R_{13}$ is from $C_1$ to $C_{12}$ branched or straight chain alkyl; substituted or unsubstituted aryl, acyl, aralkyl or $S(O)_2R_{42}$, wherein $R_{42}$ is $C_1$ to $C_{12}$ branched or straight chain alkyl; or substituted or unsubstituted aryl.

The invention further relates to a method for preparing a compound having the structure IV:

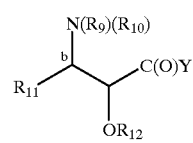

IV wherein, $R_9$ and $R_{10}$ are aralkyl;

$R_{11}$ is substituted or unsubstituted aryl;

$R_{12}$ is acyl, silyl, alkyl, aryl, or aralkyl; and

Y is $OR_{13}$, wherein $R_{13}$ is from $C_1$ to $C_{12}$ branched or straight chain alkyl; substituted or unsubstituted aryl; acyl, aralkyl, or $S(O)_2R_{42}$, wherein $R_{42}$ is $C_1$ to $C_{12}$ branched or straight chain alkyl or substituted or unsubstituted aryl, comprising:

(a) admixing abase and a compound having the structure IX:

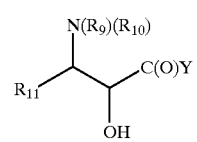

IX wherein, $R_9$ and $R_{10}$ are aralkyl;

$R_{11}$ is substituted or unsubstituted aryl; and

Y is $OR_{13}$, wherein $R_{13}$ is from $C_1$ to $C_{12}$ branched or straight chain alkyl; or substituted or unsubstituted aryl, acyl, aralkyl, or $S(O)_2R_{42}$, wherein $R_{42}$ is $C_1$ to $C_{12}$ branched or straight chain alkyl; or substituted or unsubstituted aryl, to produce an intermediate, and (b) admixing the intermediate of step (a) with an esterification agent, a silylating agent, or an alkylating agent.

The invention further relates to a method for preparing an ester, comprising admixing a compound having the structure VII:

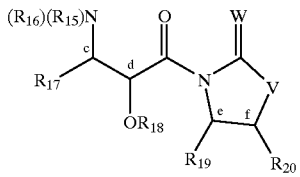

VII wherein, $R_{15}$ and $R_{16}$ are, independently, hydrogen, $Si(R_{21})_3$ or $C(O)R_{22}$, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is hydrogen; branched or straight chain $C_1$–$C_{12}$ alkyl; unsubstituted or substituted aryl; aralkyl; $Si(R_{28})_3$ or $C(O)R_{29}$, wherein, each $R_{28}$ is, independently, branched or straight chain $C_1$–$C_{12}$ alkyl; or aralkyl;

$R_{29}$ is substituted or unsubstituted aryl, aralkyl or from $C_1$–$C_{12}$ branched or straight chain alkyl;

$R_{19}$ and $R_{20}$ are, independently, branched or straight chain $C_1$–$C_{12}$ alkyl, aryl, aralkyl, or $C(O)OR_{30}$, wherein $R_{19}$ is not hydrogen;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl, with an alkoxide.

The invention further relates to a method for preparing a compound having the structure VII:

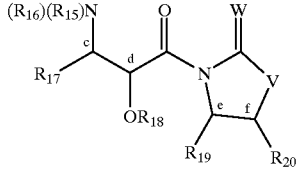

VII wherein, $R_{15}$ and $R_{16}$ are, independently, hydrogen, $Si(R_{21})_3$ or $C(O)R_{22}$, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is branched or straight chain $C_1$–$C_{12}$ alkyl; unsubstituted or substituted aryl; aralkyl; $Si(R_{28})_3$ or $C(O)R_{29}$, wherein, each $R_{28}$ is, independently, branched or straight chain $C_1$–$C_{12}$ alkyl; or aralkyl;

$R_{29}$ is substituted or unsubstituted aryl, aralkyl or from $C_1$–$C_{12}$ branched or straight chain alkyl;

$R_{19}$ and $R_{20}$ are, independently, branched or straight chain $C_1$–$C_{12}$ alkyl, aryl, aralkyl, or $C(O)OR_{30}$, wherein $R_{19}$ is not hydrogen;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl, comprising,
(a) admixing
(i) a compound having the structure X

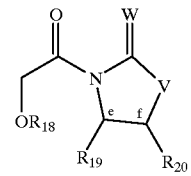

X wherein $R_{18}$–$R_{20}$ are as above,
(ii) a Lewis acid; and
(iii) a base,
to produce a first intermediate;
(b) reacting the first intermediate of step (a) with a compound having the structure XI:

XI wherein $R_{15}$ and $R_{17}$ are as above,
to produce a second intermediate; and
(c) admixing the second intermediate of step (b) with a proton source.

The invention further relates to a compound having the structure VII:

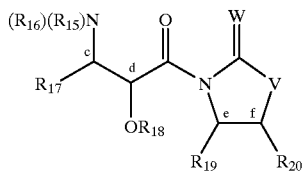

VII wherein, $R_{15}$ and $R_{16}$ are, independently, hydrogen, $Si(R_{21})_3$ or $C(O)R_{22}$, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is hydrogen; branched or straight chain $C_1$–$C_{12}$ alkyl; unsubstituted or substituted aryl; aralkyl; $Si(R_{28})_3$ or $C(O)R_{29}$, wherein, each $R_{28}$ is, independently, branched or straight chain $C_1$–$C_{12}$ alkyl; or aralkyl;

$R_{29}$ is substituted or unsubstituted aryl, aralkyl or from $C_1$–$C_{12}$ branched or straight chain alkyl;

$R_{19}$ and $R_{20}$ are, independently, branched or straight chain $C_1$–$C_{12}$ alkyl, aryl, aralkyl, or $C(O)OR_{30}$, wherein $R_{19}$ is not hydrogen;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl.

The invention further relates to a method for preparing a compound having the structure VII:

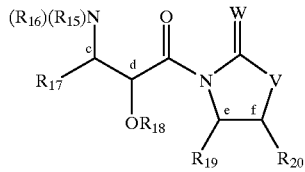

VII wherein, $R_{15}$ and $R_{16}$ are, independently, hydrogen, $Si(R_{21})_3$ or $C(O)OMe$, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is hydrogen:

$R_{19}$ and $R_{20}$ are, independently, branched or straight chain $C_1$–$C_{12}$ alkyl, aryl, aralkyl, or $C(O)OR_{30}$, wherein $R_{19}$ is not hydrogen;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl, comprising, (a) admixing
   (i) a compound having the structure XIII

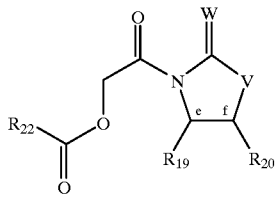

XIII wherein $R_{19}$–$R_{20}$ and $R_{22}$ are as above,
   (ii) a Lewis acid; and
   (iii) a first base,
to produce a first intermediate;

(b) reacting the first intermediate of step (a) with a compound having the structure XI:

XI wherein $R_{15}$ and $R_{17}$ are as above,
to produce a second intermediate; and (c) admixing the second intermediate with a basic buffer, wherein the buffer comprises a second base.

The invention further relates a compound having the structure XIV or XV:

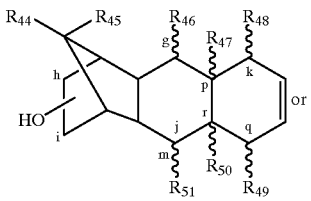

XIV

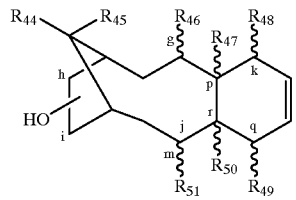

XV wherein, $R_{44}$ and $R_{45}$ are, independently, hydrogen; $C_1$–$C_{12}$ branched or straight chain alkyl; or $R_{44}$ and $R_{45}$ art part of a cycloaliphatic group;

when g is a single bond, $R_{46}$ is hydroxy; acetyl; or $C_1$–$C_{12}$ branched or straight chain alkoxy;

when g is a double bond, $R_{46}$ is oxygen;

$R_{47}$ is a $C_1$–$C_{12}$ branched or straight chain alkyl ester; $C_1$–$C_{12}$ branched or straight chain alkyl; carboalkoxy; hydroxyalkyl; or derivatized or protected hydroxyalkyl;

$R_{48}$ is $C_1$–$C_{12}$ branched or straight chain alkyl; substituted or unsubstituted aryl; acetyl; hydroxyalkyl; or derivatized or protected hydroxyalkyl;

$R_{49}$ and $R_{50}$ are, independently, hydrogen; $C_1$–$C_{12}$ branched or straight chain alkyl or alkoxy; or acetyl, provided that when one of $R_{49}$ or $R_{50}$ is hydrogen, the other of $R_{49}$ and $R_{50}$ is not hydrogen;

when m is a double bond, $R_{51}$ is oxygen;

when m is a single bond, $R_{51}$ is OH or $OC(O)R_{52}$, wherein $R_{52}$ is substituted or unsubstituted aryl; or cycloaliphatic; and the hydroxyl group is located at carbon h or i.

None of the references described above disclose the methods and compounds of the present invention. Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the examples included therein.

Before the present compositions of matter and methods are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

The singular forms "a," "an" and "the" include plural referents unless the context clearly dictates otherwise.

Throughout the application, the term "compound" refers to all compounds embodied by the designated structure in the present application. For example, compound I refers to all compounds having the structure I as defined in the application.

The term "aralkyl" is defined as any group that has one or more aliphatic or cycloaliphatic groups attached to an aromatic ring.

The term "cyclization agent" is defined as an agent that activates a hydroxyl group and renders the carbon attached to it more susceptible to internal nucleophilic attack.

The term "esterification agent" is defined as any agent that will catalyze the formation of an ester from an alcohol or alkoxide and a carboxylic acid.

Esterification of Alcohols—Part I

In accordance with the purpose(s) of this invention, as embodied and broadly described herein, this invention, in one aspect, relates to a method for preparing an ester, comprising:

(a) admixing a compound having the structure I:

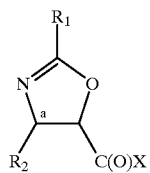

wherein,
$R_1$ and $R_2$ are, independently, from $C_1$ to $C_{12}$ branched or straight chain alkyl; or substituted or unsubstituted aryl; and X is a halogen or $OR_3$, wherein $R_3$ is from $C_1$ to $C_{12}$ branched or straight chain alkyl; substituted or unsubstituted aryl; aralkyl; acyl, or $S(O)_2R_{41}$, wherein $R_{41}$ is $C_1$ to $C_{12}$ branched or straight chain alkyl; or substituted or unsubstituted aryl, with abase to form an intermediate; and (b) admixing the intermediate of step (a) with an alcohol, an alkoxide, or a combination thereof.

The invention further relates to a method for preparing an ester, comprising admixing a compound having the structure III:

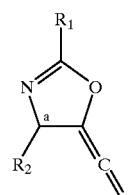

wherein, $R_1$ and $R_2$ are, independently, from $C_1$ to $C_{12}$ branched or straight chain alkyl or substituted or unsubstituted aryl, with an alcohol, an alkoxide or a combination thereof.

The invention further relates to a method for preparing an ester, comprising admixing:

(a) a base;

(b) an alcohol, an alkoxide or a combination thereof; and (c) a compound having the structure I:

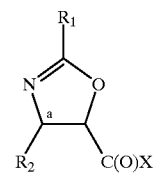

wherein, $R_1$ and $R_2$ are, independently, from $C_1$ to $C_{12}$ branched or straight chain alkyl; or substituted or unsubstituted aryl; and X is a halogen or $OR_3$, wherein $R_3$ is from $C_1$ to $C_{12}$ branched or straight chain alkyl; substituted or unsubstituted aryl; aralkyl; acyl, or $S(O)_2R_{41}$, wherein $R_{41}$ is $C_1$ to $C_{12}$ branched or straight chain alkyl; or substituted or unsubstituted aryl.

The invention further relates to a method for preparing an ester, comprising admixing:

(a) a base;

(b) an alcohol, an alkoxide or a combination thereof; and (c) a compound having the structure IV:

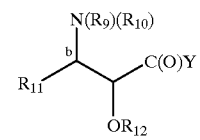

wherein, $R_9$ and $R_{10}$ are, independently, an aralkyl or $C(O)R_{31}$, wherein $R_{31}$ is $C_1$ to $C_{12}$ straight chain or branched alkyl; substituted or unsubstituted aryl; or aralkyl;

$R_{11}$ is from $C_1$ to $C_{12}$ branched or straight chain alkyl or substituted or unsubstituted aryl;

$R_{12}$ is silyl, alkyl, acyl, aryl, or aralkyl; and

Y is a halogen or $OR_{13}$, wherein $R_{13}$ is from $C_1$ to $C_{12}$ branched or straight chain alkyl; substituted or unsubstituted aryl; aralkyl; acyl; or $S(O)_2R_{42}$, wherein $R_{42}$ is $C_1$ to $C_{12}$ straight chain or branched alkyl; substituted or unsubstituted aryl The invention further relates to a method for preparing an ester, comprising admixing:

(a) an alcohol, an alkoxide, or a combination thereof; and (b) a compound having the structure V:

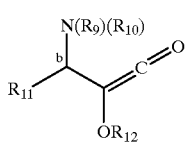

V wherein,
$R_9$ and $R_{10}$ are, independently, an aralkyl or $C(O)R_{31}$, wherein $R_{31}$ is $C_1$ to $C_{12}$ straight chain or branched alkyl; substituted or unsubstituted aryl; or aralkyl;
$R_{11}$ is from $C_1$ to $C_{12}$ branched or straight chain alkyl or substituted or unsubstituted aryl; and
$R_{12}$ is silyl, alkyl, aryl, aralkyl or acyl.

The applicants have discovered that the combination of a base, an alcohol, and compound I or IV results in the formation of an ester. In one embodiment, the base can be added to a mixture of the alcohol and compound I and IV. In a preferred embodiment, compound I or IV is treated with a base, followed by the addition of the alcohol.

Without wishing to be bound by theory, it is believed that when the base and compound I or IV are combined together, the ketene complexes III and V are produced, respectively. It is believed that the base deprotonates a hydrogen at the α-carbon (the carbon adjacent to the C(O)X group) of I and IV with concomitant loss of the leaving group, X and Y, respectively, to generate the ketene complex. The ketene complexes III and V are highly electrophilic; thus, they are susceptible to nucleophilic attack. When a ketene is treated with an alcohol of the present invention, the alcohol reacts at C1 of the ketene to produce the corresponding ester (eq. 1). In another embodiment, an alkoxide will react with the ketene to generate the ester. In the present invention, the ketene complexes III and V are not isolated, but generated in situ prior to the addition of the alcohol.

eq. 1

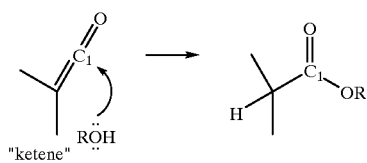

The bases useful for generating the ketene complexes of the present invention include, but are not limited to, an amide, a secondary amine or a tertiary amine. An amide is defined herein as $(R)_2N^\ominus$, wherein each R is preferably an aliphatic group, a cycloaliphatic group, or a silyl group. Examples of amides useful in the present invention include, but are not limited to, potassium hexamethyldisilazide, sodium hexamethyldisilazide, lithium diisopropylamide, lithium hexamethyldisilazide, and lithium 2,2,6,6-tetramethylpiperidine. An examples of a secondary amine includes, but is not limited to, 2,2,6,6-tetramethylpiperidine. Examples of tertiary amines include, but are not limited to, dimethyl ethyl amine, triethylamine and pyridine.

One advantage of the present invention is that the stereochemistry at C2 of compounds I and IV does not have to be set. Thus, the stereochemistry at C2 can be S or R. When I-trans and I-cis are treated with a base (Scheme I), deprotonation at C2 and subsequent loss of X results in the formation of the ketene complex III. Thus, the applicants have discovered that the cis and trans isomers of I and IV can be used to esterify an alcohol, which is highly desirable and nowhere taught, suggested or otherwise motivated in the art.

Scheme I

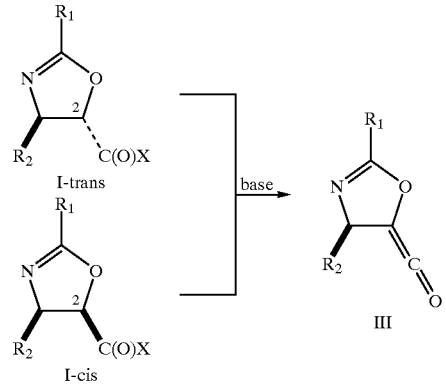

Another advantage of the present method is that once the ketene complexes III and V are generated, nucleophilic attack by the alcohol or alkoxide can occur diasteroselectively. In one embodiment, in the case of the acyclic ketene complex V, nucleophilic attack by the alcohol or alkoxide will most likely occur opposite or anti to the adjacent R group at $C_b$ of V. In another embodiment, in the case of the cyclic ketene complex III, nucleophilic attack by the alcohol or alkoxide can occur anti or syn to the adjacent R group at $C_a$; however, due to thermodynamic considerations, the trans ester is the predominant product formed. Thus, by varying the stereochemistry at $C_a$ and $C_b$, it is possible to generate optically active esters using this method of the present invention. This feature of the present invention is very useful with respect to the synthesis of biologically active compounds that possess ester groups.

In one embodiment, a compound having the structure I can be used to esterify an alcohol. In the case of compound I, $R_1$ and $R_2$ are, independently, from $C_1$ to $C_{12}$ branched or straight chain alkyl or substituted or unsubstituted aryl; and X is a halogen or $OR_3$, wherein $R_3$ is from $C_1$ to $C_{12}$ branched or straight chain alkyl; substituted or unsubstituted aryl; aralkyl; acyl, or $S(O)_2R_{41}$, wherein $R_{41}$ is $C_1$ to $C_{12}$ branched or straight chain alkyl or substituted or unsubstituted aryl. Throughout the application, the alkyl group is from $C_1$ to $C_{12}$ branched or straight chain alkyl, preferably from $C_1$ to $C_6$ branched or straight chain alkyl, and more preferably from $C_1$ to $C_4$ branched or straight chain alkyl. The term "acyl" is defined as a group having the structure R'(O)CO, wherein R' is alkyl, aryl, or aralkyl. Acyl groups useful in the present invention include, but are not limited to, acetyl and benzoyl. The term "aralkyl" is defined as any group that has one or more aliphatic or cycloaliphatic groups attached to an aromatic ring. Examples of an aralkyl group of the present invention include, but are not limited to, benzyl and p-nitrobenzyl groups. In one embodiment, $R_1$ and $R_2$ are phenyl; $R_3$ is methyl; and the stereochemistry at a is S. In another embodiment, $R_1$ and $R_2$ are phenyl; $R_3$ is isopropyl; and the stereochemistry at a is S. In yet another embodiment, $R_1$ and $R_2$ are phenyl; $R_3$ is tert-butyl; and the stereochemistry at a is S.

The invention further relates to a method for preparing a compound having the structure I:

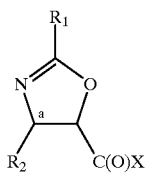

I wherein,

R$_1$ and R$_2$ are, independently, from C$_1$ to C$_{12}$ branched or straight chain alkyl or substituted or unsubstituted aryl; and X is OR$_3$, wherein R$_3$ is from C$_1$ to C$_{12}$ branched or straight chain alkyl; substituted or unsubstituted aryl; aralkyl; acyl, or S(O)$_2$R$_{41}$, wherein R$_{41}$ is C$_1$ to C$_{12}$ branched or straight chain alkyl; or substituted or unsubstituted aryl, and R$_2$ and C(O)X are cis to one another, comprising:

(a) admixing a compound having the structure VI:

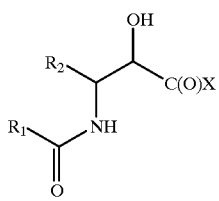

VI wherein,

R$_1$ and R$_2$ are, independently, from C$_1$ to C$_{12}$ branched or straight chain alkyl or substituted or unsubstituted aryl;

X is OR$_3$, wherein R$_3$ is from C$_1$ to C$_{12}$ branched or straight chain alkyl; substituted or unsubstituted aryl; aralkyl; acyl, or S(O)$_2$R$_{41}$, wherein R$_{41}$ is C$_1$ to C$_{12}$ branched or straight chain alkyl; or substituted or unsubstituted aryl; and the hydroxyl group and amide group are cis to one another, with a cyclization agent.

The applicants have discovered a method for preparing a compound having the structure I, wherein R$_2$ and C(O)X are cis to one another. The cis and trans isomers of compound I are shown in Scheme I. The art heretofore only disclosed a method for making the trans isomer of compound I.

The use of a cyclization agent is necessary to cyclize compound VI to compound I. An example of a cyclization agent useful in the present invention is triflic anhydride with pyridine. Experimental conditions for the production of I via the cyclization of VI are outlined in the forthcoming examples.

The invention further relates to a compound having the formula I:

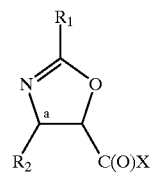

I wherein,

R$_1$ and R$_2$ are, independently, from C$_1$ to C$_{12}$ branched or straight chain alkyl or substituted or unsubstituted aryl;

X is OR$_3$, wherein R$_3$ is halogen; C$_1$ to C$_{12}$ branched or straight chain alkyl; substituted or unsubstituted aryl; aralkyl; acyl, or S(O)$_2$R$_{41}$, wherein R$_{41}$ is C$_1$ to C$_{12}$ branched or straight chain alkyl; or substituted or unsubstituted aryl; and R$_2$ and C(O)X are cis to one another.

Compounds having the structure I, wherein the compound is the cis isomer, are not disclosed in the art. In one embodiment, R$_1$ and R$_2$ are phenyl; R$_3$ is methyl; and the stereochemistry at a is S. In another embodiment, R$_1$ and R$_2$ are phenyl; R$_3$ is tert-butyl; and the stereochemistry at a is S. In another embodiment, R$_1$ and R$_2$ are phenyl; R$_3$ is isopropyl; and the stereochemistry at a is S. In another embodiment, R$_1$ and R$_2$ are phenyl; R$_3$ is phenyl; and the stereochemistry at a is S. In another embodiment, R$_1$ and R$_2$ are phenyl; R$_3$ is 2,3-dimethyl propyl, wherein the stereochemistry at the 2-position is S; and the stereochemistry at a is S.

In another embodiment, compound IV can be used to esterify an alcohol. In this case, R$_9$ and R$_{10}$ are, independently, an aralkyl or C(O)R$_{31}$, wherein R$_{31}$ is C$_1$ to C$_{12}$ straight chain or branched alkyl; substituted or unsubstituted aryl; or aralkyl; R$_{11}$ is from C$_1$ to C$_{12}$ branched or straight chain alkyl or substituted or unsubstituted aryl; R$_{12}$ is silyl; alkyl; aryl; acyl; or aralkyl; and Y is a halogen or OR$_{13}$, wherein R$_{13}$ is from C$_1$ to C$_{12}$ branched or straight chain alkyl or substituted or unsubstituted aryl, acyl, aralkyl or S(O)$_2$R$_{42}$, wherein R$_{42}$ is C$_1$ to C$_{12}$ branched or straight chain alkyl or substituted or unsubstituted aryl. In one embodiment, R$_9$ is benzyl; R$_{10}$ is α-methyl benzyl; R$_{11}$ is phenyl; R$_{12}$ is C(O)Ph; R$_{13}$ is tert-butyl; and the stereochemistry at b is S. In another embodiment, R$_9$ is benzyl; R$_{10}$ is α-methyl benzyl; R$_{11}$ is phenyl; R$_{12}$ is C(O)Ph; R$_{13}$ is methyl; and the stereochemistry at b is S. In yet another embodiment, R$_9$ is benzyl; R$_{10}$ is α-methyl benzyl; R$_{11}$ is phenyl; R$_{12}$ is C(O)Ph; Y is chloride; and the stereochemistry at b is S. As described above, the stereochemistry at C2 does not have to be set; therefore, NR$_9$R$_{10}$ and OR$_{12}$ can be syn or anti to one another.

The invention further relates to a method for preparing a compound having the structure IV:

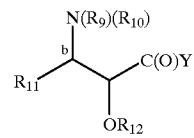

IV wherein,

R$_9$ and R$_{10}$ are aralkyl;

R$_{11}$ is substituted or unsubstituted aryl;

R$_{12}$ is acyl, silyl, alkyl, aryl, or aralkyl; and

Y is $OR_{13}$, wherein $R_{13}$ is from $C_1$ to $C_{12}$ branched or straight chain alkyl or substituted or unsubstituted aryl, acyl, aralkyl or $S(O)_2R_{42}$, wherein $R_{42}$ is $C_1$ to $C_{12}$ branched or straight chain alkyl or substituted or unsubstituted aryl, comprising:

(a) admixing a base and a compound having the structure IX:

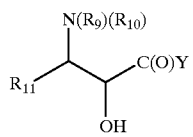

IX wherein, $R_9$ and $R_{10}$ are aralkyl;

$R_{11}$ is substituted or unsubstituted aryl; and

Y is $OR_{13}$, wherein $R_{13}$ is from $C_1$ to $C_{12}$ branched or straight chain alkyl; or substituted or unsubstituted aryl, acyl, aralkyl, or $S(O)_2R_{42}$, wherein $R_{42}$ is $C_1$ to $C_{12}$ branched or straight chain alkyl; or substituted or unsubstituted aryl, to produce an intermediate, and (b) admixing the intermediate of step (a) with an esterification agent, a silylating agent, or an alkylating agent.

Treatment of compound IX with a base results in deprotonation of the hydroxyl proton to generate the corresponding alkoxide. The alkoxide is referred to as the intermediate recited above. The alkoxide is not isolated, but subsequently treated with an esterification agent, a silylating agent, or an alkylating agent to produce compound IV. The term "esterification agent" is defined as any agent that will react with an alkoxide to produce an ester. Examples of esterification agents useful in the present invention include, but are not limited to, organic anhydrides and acyl halides. In one embodiment, the esterification agent is benzoyl chloride.

The base employed is any compound capable of deprotonating a hydroxyl group. Bases used to generate the ketene compounds III and V, such as amides, secondary and tertiary amines, are suitable for deprotonation of the hydroxyl group of IX. In one embodiment, triethyl amine can be used as the base. The experimental conditions for preparing compound IV are presented in the forthcoming examples.

The invention further relates to a compound having the structure IV:

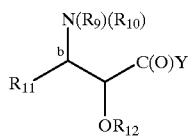

IV wherein, $R_9$ and $R_{10}$ are aralkyl;

$R_{11}$ is substituted or unsubstituted aryl;

$R_{12}$ is acyl, silyl, alkyl, aryl or aralkyl; and

Y is a halogen or $OR_{13}$, wherein $R_{13}$ is from $C_1$ to $C_{12}$ branched or straight chain alkyl or substituted or unsubstituted aryl, acyl, aralkyl, or $S(O)_2R_{42}$, wherein $R_{42}$ is $C_1$ to $C_{12}$ branched or straight chain alkyl; or substituted or unsubstituted aryl.

In one embodiment, $R_9$ is benzyl; $R_{10}$ is α-methyl benzyl; $R_{11}$ is phenyl; $R_{12}$ is C(O)Ph; and Y is tert-butoxy. In another embodiment, $R_9$ is benzyl; $R_{10}$ is α-methyl benzyl; $R_{11}$ is phenyl; $R_{12}$ is C(O)Ph; and Y is methoxy.

Once the ketene complexes III and V have been generated, the addition of an alcohol or an alkoxide will result in the formation of an ester. The applicants have discovered that a wide variety of alcohols can be added to the ketene compounds III and V to produce the corresponding ester. Alcohols useful in the present invention include, but are not limited to, aliphatic alcohols, aromatic alcohols, cycloaliphatic alcohols, or heteroaromatic alcohols. In a preferred embodiment, the alcohol is a cycloaliphatic alcohol. In another embodiment, the alcohol is (2S)-hydroxy-3-methylbutane.

In another preferred embodiment, the alcohol is a compound having the structure II:

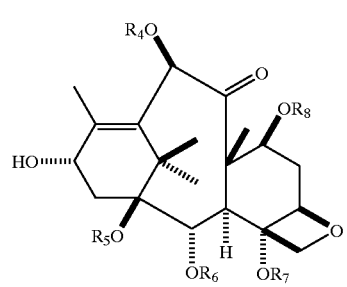

(II)

wherein, $R_4$ is acetyl or hydrogen;

$R_5$ is hydrogen;

$R_6$ is benzoyl;

$R_7$ is acetyl; and $R_8$ is hydrogen, $SiEt_3$ or $C(O)CH_2CCl_3$.

As described above, it is advantageous to efficiently attach a side chain to the hydroxyl group at the C-13 position of baccatin and derivatives thereof. In one embodiment, for compound II, $R_4$ and $R_5$ are hydrogen; $R_6$ is benzoyl; $R_7$ is acetyl; and $R_8$ is hydrogen, $SiEt_3$ or $C(O)CH_2CCl_3$. This alcohol is the precursor to taxotere. In another embodiment, $R_4$ and $R_7$ are acetyl; $R_5$ is hydrogen; $R_6$ is benzoyl; and $R_8$ is hydrogen, $SiEt_3$ or $C(O)CH_2CCl_3$. This alcohol is the precursor to Taxol.

The invention further relates a compound having the structure XIV or XV:

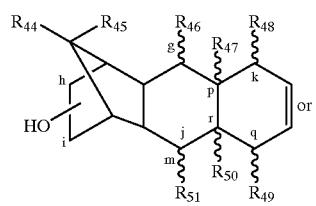

XIV

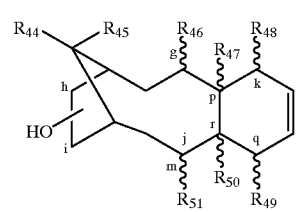

XV wherein, $R_{44}$ and $R_{45}$ are, independently, hydrogen; $C_1$–$C_{12}$ branched or straight chain alkyl; or $R_{44}$ and $R_{45}$ are part of a cycloaliphatic group;

when g is a single bond, $R_{46}$ is hydroxy; acetyl; or $C_1$–$C_{12}$ branched or straight chain alkoxy;

when g is a double bond, $R_{46}$ is oxygen;

$R_{47}$ is a $C_1$–$C_{12}$ branched or straight chain alkyl ester; $C_1$–$C_{12}$ branched or straight chain alkyl; carboalkoxy; hydroxyalkyl; or derivatized or protected hydroxyalkyl;

$R_{48}$ is $C_1$–$C_{12}$ branched or straight chain alkyl; substituted or unsubstituted aryl; acetyl; hydroxyalkyl; or derivatized or protected hydroxyalkyl;

$R_{49}$ and $R_{50}$ are, independently, hydrogen; $C_1$–$C_{12}$ branched or straight chain alkyl or alkoxy; or acetyl, provided that when one of $R_{49}$ or $R_{50}$ is hydrogen, the other of $R_{49}$ and $R_{50}$ is not hydrogen;

when m is a double bond, $R_{51}$ is oxygen;

when m is a single bond, $R_{51}$ is OH or $OC(O)R_{52}$, wherein $R_{52}$ is substituted or unsubstituted aryl; or cycloaliphatic; and the hydroxyl group is located at carbon h or i.

Applicants have discovered that compounds having the structure XIV and XV are structurally simplified analogs of Taxol with incorporated structural elements of Taxol which can embody Taxol's biological activity. Due to the difficulty in synthesizing Taxol, simplified analogs could be advantageous over semi-synthetic analogs of Taxol. The hydroxy group can be positioned at either carbon h or i, and the stereochemistry at these positions can be either R or S. In one embodiment, the hydroxyl group is at carbon h, and the stereochemistry at carbon h is S. In another embodiment, the hydroxyl group is at carbon h, and the stereochemistry at carbon h is R. In another embodiment, the hydroxyl group is at carbon i, and the stereochemistry at carbon i is S. In another embodiment, the hydroxyl group is at carbon i, and the stereochemistry at carbon i is R.

In another embodiment, $R_{44}$ and $R_{45}$ of compounds XIV and XV are independently, hydrogen or methyl, preferably hydrogen and methyl. In another embodiment, $R_{44}$ and $R_{45}$ are part of a cycloaliphatic group, wherein the cycloaliphatic group can be cyclopropyl, cyclobutyl, cyclopentyl, or cyclohexyl. In one embodiment, the cycloaliphatic group is a cyclopropyl group. In another embodiment, $R_{47}$ is methyl ester or methyl. In another embodiment, $R_{48}$ is hydroxy, ethoxy, propoxy, or derivatized or protected hydroxy. The term "derivatized or protected hydroxy" refers to hydroxyl group that has been converted to a alkoxy group, an aryloxy group, an aralkoxy group, an acyloxy group or a silyloxy group. In another embodiment, m is a single bond and $R_{52}$ is phenyl or cyclohexyl.

In one embodiment, when the compound has the structure XIV, $R_{44}$ and $R_{45}$ are hydrogen; g is a double bond; $R_{47}$ is C(O)OMe; the stereochemistry at carbon p is R; $R_{48}$ is methyl; the stereochemistry at carbon k is S; $R_{48}$ is methyl; $R_{49}$ is methyl; the stereochemistry at carbon q is R; $R_{50}$ is hydrogen; the stereochemistry at carbon r is S; m is a single bond; $R_{51}$ is OC(O)Ph; the stereochemistry at carbon j is R; and the hydroxyl group is at carbon h or i. In another embodiment, the hydroxyl group is at carbon h and the stereochemistry at carbon h is R. In another embodiment, the hydroxyl group is at carbon h and the stereochemistry at carbon h is S. In another embodiment, the hydroxyl group is at carbon i and the stereochemistry is S.

In one embodiment, when the compound has the structure XIV, $R_{44}$ and $R_{45}$ are hydrogen; g is a double bond; $R_{47}$ is C(O)OMe; the stereochemistry at carbon p is R; $R_{48}$ is methyl; the stereochemistry at carbon k is S; $R_{49}$ is methyl; the stereochemistry at carbon q is R; $R_{50}$ is hydrogen; the stereochemistry at carbon r is S; m is a double bond; and the hydroxyl group is at carbon h or i. In another embodiment, the hydroxyl group is at carbon h and the stereochemistry at carbon h is R. In another embodiment, the hydroxyl group is at carbon h and the stereochemistry at carbon h is S. In another embodiment, the hydroxyl group is at carbon i and the stereochemistry at carbon i is S.

Procedures for preparing compounds XIV and XV are provided in the forthcoming examples. Using the process of the present invention, compounds XIV and XV can be used to esterify alcohols.

In another embodiment, the corresponding alkoxide of the alcohols described above will also generate an ester when used in the process of the present invention. Any base that is capable of deprotonating a hydroxyl proton to produce the corresponding oxide anion is suitable in the present invention. Bases useful in the present invention include, but are not limited to, potassium hexamethyldisilazide, sodium hexamethyldisilazide, triethylamine, lithium diisopropylamide, lithium hexamethyldisilazide, dimethylethylamine, potassium hydride, sodium hydride or lithium 2,2,6,6-tetramethylpiperidine.

The present invention also provides a process for the esterification of an alcohol and/or an alkoxide that does not require the use of harsh reaction conditions (i.e. elevated temperature, extended reactions times). In one embodiment, the base is initially added to compound I or IV prior to the addition of the alcohol or alkoxide. In one embodiment, the amount of base used is less than the amount of compound I or IV. In a preferred embodiment, an excess amount of base is used relative to the amount of compound I or IV. In the case of compound I, the amount of base employed is from 1 to 10 equivalents, preferably 1 to 1.5 equivalents to 1 equivalent compound I. In another embodiment, when compound IV is used, the amount of base used is from 1 to 10 equivalents to 1 equivalent of compound IV. A slight excess of base relative to compounds I and IV is necessary in order to generate the corresponding ketene prior to the addition of the alcohol or alkoxide.

The process of the present invention typically involves the use of a solvent system Organic solvents known in the art are useful in the present invention. Examples of organic solvents useful in the present invention include, but are not limited to, tetrahydrofuran, diethyl ether, toluene, dimethoxyethane, t-butyl methyl ether, or a mixture thereof.

Reaction temperatures and times can vary when adding the base to compounds I and IV. In one embodiment, the base is added to compound I from −50° C. to 80° C. In another embodiment, the lower limit of the reaction temperature is −45° C., −40° C., −35° C., −30° C., −25° C., −20° C., or −15° C., and the upper limit is −5° C., −10° C., −15° C., −20° C., −25° C., 0° C., 20 ° C., 40 ° C., or 60° C. The base is allowed to react with compound I or IV at from 30 seconds to 3 hours. In another embodiment, the lower time limit can be 1, 5, 10, 15 minutes, and the upper limit can be 2 hours, 1 hour, 30 minutes, 15 minutes, 10 minutes, or 5 minutes.

Once the ketene complexes III and V have been generated in situ, an alcohol, alkoxide, or a combination thereof is added. The amount of the alcohol or alkoxide can be from 1 to 3 equivalents, preferably from 1 to 2 equivalents, and more preferably from 1 to 1.2 equivalents. The alcohol or alkoxide is allowed to react with the ketene at from 15 minutes to 24 hours, preferably from 15 minutes to 2 hours. In another embodiment, the lower time limit can be 20, 25, 30, 40 or 50 minutes, and the upper limit can be 1 hour, 45 minutes; 1 hour, 30 minutes; 1 hour; or 45 minutes. The temperature at which the alcohol and/or alkoxide can be added to the ketene can be from −50° C. to 23° C. In another embodiment, the lower temperature limit can be −45° C., −40° C., −35° C., −30° C., −25° C. or −20° C.; and the lower limit can be 20° C., 15° C., 10° C., 5° C., 0° C., −5° C., −10° C. or −20° C.

Esterification of Alcohols—Parts II

In accordance with the purpose(s) of this invention, as embodied and broadly described herein, this invention, in one aspect, relates to a method for preparing an ester, comprising admixing a compound having the structure VII:

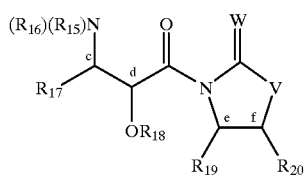

VII wherein, $R_{15}$ and $R_{16}$ are, independently, hydrogen, $Si(R_{21})_3$ or $C(O)R_{22}$, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is hydrogen; branched or straight chain $C_1$–$C_{12}$ alkyl; unsubstituted or substituted aryl; aralkyl; $Si(R_{28})_3$ or $C(O)R_{29}$, wherein, each $R_{28}$ is, independently, branched or straight chain $C_1$–$C_{12}$ alkyl; or aralkyl;

$R_{29}$ is substituted or unsubstituted aryl, aralkyl or from $C_1$–$C_{12}$ branched or straight chain alkyl;

$R_{19}$ and $R_{20}$ are, independently, branched or straight chain $C_1$–$C_{12}$ alkyl, aryl, aralkyl, or $C(O)OR_{30}$, wherein $R_{19}$ is not hydrogen;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl, with an alkoxide.

The alkoxide is prepared in situ by treating the corresponding alcohol with a base. Bases useful in generating the alkoxide include, but are not limited to amides, secondary and tertiary amines. In a preferred embodiment, lithium hexamethyldisilazide, sodium hexamethyldisilazide, potassium hexamethyldisilazide, n-butyllithium, sodium hydride, potassium hydride or lithium diisopropylamide can be used. Once the alkoxide is produced, it can react with compound VII to generate an ester. Nucleophilic attack at the carbamide followed by the loss of the heterocyclic ring results in the formation of the ester.

The method of the present invention has a number of advantages. First, by varying the stereochemistry of $R_{19}$ and $R_{20}$ of compound VII, it is possible to control the diasteroselectivity of the condensation reaction between the alkoxide and compound VII. Second, by varying V and W of compound VII, it is possible to enhance or increase the reaction between the alkoxide and compound VII. In one embodiment, V and W are sulfur. In another embodiment, $R_{17}$ is phenyl and $R_{18}$ is benzoyl. Finally, it is possible to recover the oxazolidine ring and reuse it after the condensation reaction.

All of the alcohols described above can be converted to the corresponding alkoxide and used in the present invention. In one embodiment, the alkoxide is a compound having the structure VIII:

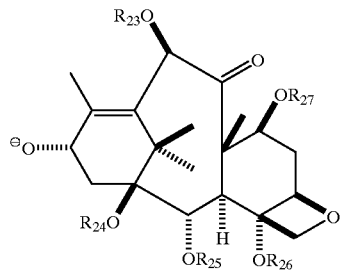

(VIII)

wherein, $R_{23}$ is acetyl or hydrogen;

$R_{24}$ is hydrogen;

$R_{25}$ is benzoyl;

$R_{26}$ is acetyl; and $R_{27}$ is hydrogen, $SiEt_3$ or $C(O)CH_2CCl_3$.

As described above, an efficient method for attaching a side chain at the C-13 position of baccatin or derivatives thereof is not known in the art; thus, the applicants have discovered another method for attaching a side chain to precursors of taxol and derivatives thereof. In one embodiment, for compound VIII, $R_{23}$ and $R_{24}$ are hydrogen; $R_{25}$ is benzoyl; $R_{26}$ is acetyl; and $R_{27}$ is hydrogen, $SiEt_3$ or $C(O)CH_2CCl_3$. This alkoxide is the precursor to taxotere. In another embodiment, $R_{23}$ and $R_{26}$ are acetyl; $R_{24}$ is hydrogen; $R_{25}$ is benzoyl; and $R_{27}$ is hydrogen, $SiEt_3$ or $C(O)CH_2CCl_3$. This alkoxide is a precursor to Taxol.

In another embodiment, the alkoxide is a compound having the structure XVI or XVII:

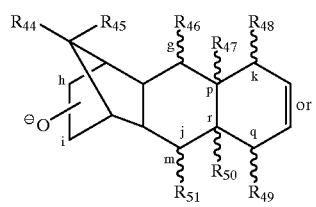

XVI

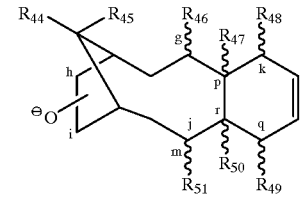

XVII wherein, $R_{44}$ and $R_{45}$ are, independently, hydrogen; $C_1$–$C_{12}$ branched or straight chain alkyl; or $R_{44}$ and $R_{45}$ are part of a cycloaliphatic group;

when g is a single bond, $R_{46}$ is hydroxy; acetyl; or $C_1$–$C_{12}$ branched or straight chain alkoxy;

when g is a double bond, $R_{46}$ is oxygen;

$R_{47}$ is a $C_1$–$C_{12}$ branched or straight chain alkyl ester; $C_1$–$C_{12}$ branched or straight chain alkyl; carboalkoxy; hydroxyalkyl; or derivatized or protected hydroxyalkyl;

R$_{48}$ is C$_1$–C$_{12}$ branched or straight chain alkyl; substituted or unsubstituted aryl; acetyl; hydroxyalkyl; or derivatized or protected hydroxyalkyl;

R$_{49}$ and R$_{50}$ are, independently, hydrogen; C$_1$–C$_{12}$ branched or straight chain alkyl or alkoxy; or acetyl, provided that when one of R$_{49}$ or R$_{50}$ is hydrogen, then the other of R$_{49}$ and R$_{50}$ is not hydrogen;

when m is a double bond, R$_{51}$ is oxygen;

when m is a single bond, R$_{51}$ is OC(O)R$_{52}$, wherein R$_{52}$ is substituted or unsubstituted aryl; or cycloaliphatic; and the hydroxyl group is located at carbon h or i.

The invention further relates to a compound having the structure VII:

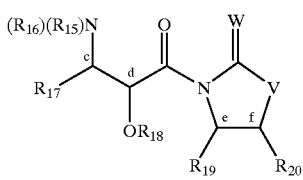

VII wherein,

R$_{15}$ and R$_{16}$ are, independently, hydrogen, Si(R$_{21}$)$_3$ or C(O)R$_{22}$, wherein each R$_{21}$ is, independently, branched or straight chain C$_1$–C$_{12}$ alkyl; and R$_{22}$ is substituted or unsubstituted aryl, aralkyl or from C$_1$–C$_{12}$ branched or straight chain alkyl;

R$_{17}$ is substituted or unsubstituted aryl, aralkyl, or from C$_1$–C$_{12}$ branched or straight chain alkyl;

R$_{18}$ is hydrogen; branched or straight chain C$_1$–C$_{12}$ alkyl; unsubstituted or substituted aryl; aralkyl; Si(R$_{28}$)$_3$ or C(O)R$_{29}$, wherein, each R$_{28}$ is, independently, branched or straight chain C$_1$–C$_{12}$ alkyl; or aralkyl;

R$_{29}$ is substituted or unsubstituted aryl, aralkyl or from C$_1$–C$_{12}$ branched or straight chain alkyl;

R$_{19}$ and R$_{20}$ are, independently, branched or straight chain C$_1$–C$_{12}$ alkyl, aryl, aralkyl, or C(O)OR$_{30}$, wherein R$_{19}$ is not hydrogen;

R$_{30}$ is branched or straight chain C$_1$–C$_{12}$ alkyl; and

V and W are, independently, sulfur, oxygen, or NR$_{43}$, wherein R$_{43}$ is hydrogen; branched or straight chain C$_1$–C$_{12}$ alkyl; or aralkyl.

The invention further relates to a method for preparing a compound having the structure VII:

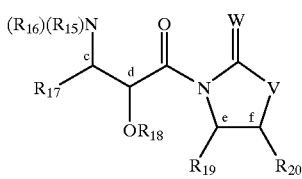

VII wherein,

R$_{15}$ and R$_{16}$ are, independently, hydrogen, Si(R$_{21}$)$_3$ or C(O)R$_{22}$, wherein each R$_{21}$ is, independently, branched or straight chain C$_1$–C$_{12}$ alkyl; and R$_{22}$ is substituted or unsubstituted aryl, aralkyl or from C$_1$–C$_{12}$ branched or straight chain alkyl;

R$_{17}$ is substituted or unsubstituted aryl, aralkyl, or from C$_1$–C$_{12}$ branched or straight chain alkyl;

R$_{18}$ is branched or straight chain C$_1$–C$_{12}$ alkyl; unsubstituted or substituted aryl; aralkyl; Si(R$_{28}$)$_3$ or C(O)R$_{29}$, wherein, each R$_{28}$ is, independently, branched or straight chain C$_1$–C$_{12}$ alkyl; or aralkyl;

R$_{29}$ is substituted or unsubstituted aryl, aralkyl or from C$_1$–C$_{12}$ branched or straight chain alkyl;

R$_{19}$ and R$_{20}$ are, independently, branched or straight chain C$_1$–C$_{12}$ alkyl, aryl, aralkyl, or C(O)OR$_{30}$, wherein R$_{19}$ is not hydrogen;

R$_{30}$ is branched or straight chain C$_1$–C$_{12}$ alkyl; and

V and W are, independently, sulfur, oxygen, or NR$_{43}$, wherein R$_{43}$ is hydrogen; branched or straight chain C$_1$–C$_{12}$ alkyl; or aralkyl, comprising, (a) admixing (i) a compound having the structure X

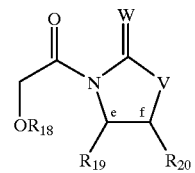

X wherein R$_{18}$–R$_{20}$ are as above, (ii) a Lewis acid; and (iii) a base, to produce a first intermediate;

(b) reacting the first intermediate of step (a) with a compound having the structure XI:

XI wherein R$_{15}$ and R$_{17}$ are as above, to produce a second intermediate; and (c) admixing the second intermediate of step (b) with a proton source.

Treatment of compound X with a Lewis acid and a base results in the formation of an enolate, which is the first intermediate recited above. In one embodiment, compound X is treated with the Lewis acid prior to the addition of the base. Bases useful for generating the enolate include, but are not limited to, potassium hexamethydisilazide, sodium hexamethydisilazide and lithium diisopropylamide. In a preferred embodiment, the base is lithium diisopropylamide. Once the enolate has been prepared in situ, it is treated with the imine compound XI. In a preferred embodiment, R$_{15}$ of the imine is C(O)Ph. The enolate reacts with the imine to generate a β-amino,α-alkoxyamide, which is the second intermediate recited above. In another embodiment, the Lewis acid facilitates the reaction between the enolate and the imine. In one embodiment, the Lewis acid is a zinc, magnesium, aluminum, boron, tin or titanium compound. In another embodiment, the Lewis acid comprises a dialkylboron triflate, stannous triflate, stannic chloride, stannous chloride or titanium tetrachloride.

Once the β-amino,α-alkoxyamide is produced, it is quenched with a proton source. Proton sources useful in the present invention include, but are not limited to, a weak acid or water.

The invention further relates to a method for preparing a compound having the structure VII:

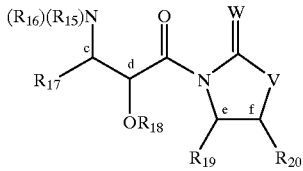

VII wherein,
$R_{15}$ and $R_{16}$ are, independently, hydrogen, $Si(R_{21})_3$ or C(O)OMe, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is hydrogen:

$R_{19}$ and $R_{20}$ are, independently, branched or straight chain $C_1$–$C_{12}$ alkyl, aryl, aralkyl, or $C(O)OR_{30}$, wherein $R_{19}$ is not hydrogen;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl, comprising,
(a) admixing
(i) a compound having the structure XIII

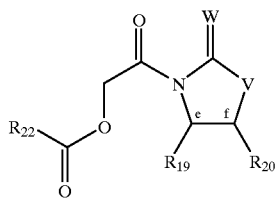

XIII wherein $R_{19}$–$R_{20}$ and $R_{22}$ are as above,
(ii) a Lewis acid; and
(iii) a first base,
to produce a first intermediate;
(b) reacting the first intermediate of step (a) with a compound having the structure XI:

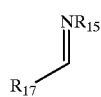

XI wherein $R_{15}$ and $R_{17}$ are as above,
to produce a second intermediate; and
(c) admixing the second intermediate with a basic buffer, wherein the buffer comprises a second base.

In a similar reaction as described above, the addition of a first base, such as an amide or secondary or tertiary amine, to compound XIII results in the formation of an enolate, which is the first intermediate recited above. Once the enolate has been produced, the imine compound XI is added to produce an β-amino,α-alkoxyamide, which is the second intermediate. The amide is then treated with a basic buffer to generate compound VII. In one embodiment, the buffer is an aqueous solution of $NaHCO_3$ or a phosphate. Upon treatment of the amide intermediate with the basic buffer, the $C(O)R_{22}$ group migrates from oxygen to nitrogen. The migration of $C(O)R_{22}$, and in particular, C(O)Ph, from oxygen to nitrogen under basic conditions is well known in the art.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, temperature is in °C. or is at room temperature and pressure is at or near atmospheric.

General Procedures

Melting points were determined on a Thomas Hoover capillary melting point apparatus and are uncorrected. IR spectra were obtained on a Nicolet Impact 400 FT-IR spectrometer using the OMNIC software package. $^1$H NMR spectra were recorded at either 300 MHz on a General Electric QE-300 or at 400 MHz on a Varian-400 spectrometer. $^{13}$C NMR were recorded at either 75 MHz on a General Electric QE-300 or at 100 MHz on a Varian-400 spectrometer. Unless otherwise stated, spectra were recorded in deuterated chloroform ($CDCl_3$) with residual chloroform ($^1$H NMR δ7.26 ppm, $^{13}$C NMR δ77.0 ppm) taken as the internal standard. Elemental analyses were performed by Atlantic Microlab Inc., P. O. Box 2288, Norcross, Ga. Mass spectra were obtained on either a VG 70-S Nier Johnson or a JEOL Mass Spectrometer, purchased through NIH and NSF as shared instruments. Analytical Thin Layer Chromatography (TLC) was performed on pre-coated glass backed plates purchased from EM Science (silica gel 60 $F_{254}$; 0.25 mm thickness). Flash chromatography was performed with silica gel 60 (230–400 mesh ASTM) from EM Science. All reactions were performed under a dry argon atmosphere in glassware which was flame-dried under vacuum unless otherwise indicated. Solvents were dried using activated 4 Å molecular sieves. Dry solvents were used unless otherwise indicated. Brine refers to a saturated aqueous solution of NaCl. Saturated $NH_4Cl$ solution refers to a saturated aqueous solution of $NH_4Cl$.

Compound 1 was prepared using a slightly modified version of the procedure previously reported by Sharpless and co-workers (*J. Org. Chem.* 1994, 59, 5104).

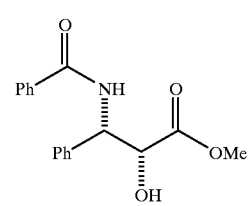

1

Synthesis of Methyl (4S,5S)-2,4-diphenyl-4,5-dihydro-oxazole-5-carboxylate (or 2,4-Diphenyl-4(S),5(S)-dihydro-oxazole-5-carboxylic acid methyl ester) (2)

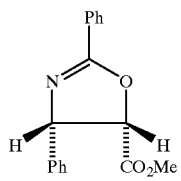

A three-necked flask was charged with 1 (2.59 g, 8.66 mmol) and dry CH$_2$Cl$_2$ (43 mL). The suspension was cooled to −30° C. and pyridine (0.84 mL, 10.4 mmol) was added. After stirring for several minutes, trifluoromethanesulfonic anhydride (1.45 mL, 8.6 mmol) was added dropwise and the reaction mixture was gradually warmed from −30° C. to 15° C. with an acetone bath. The reaction flask was then removed from the bath and was stirred at room temperature for approximately 4 hours. The reaction mixture was then poured into a saturated NaHCO$_3$ solution (45 mL) and extracted with CH$_2$Cl$_2$ (2×). The organic layers were washed with brine, dried over MgSO$_4$, filtered and evaporated. Purification by silica gel chromatography (9:1 hexanes/ethyl acetate increased to 2:1 hexanes/ethyl acetate) yielded 2.11 g (87%) of 2 as a white solid. R$_f$0.43 (4:1 hexanes/ethyl acetate); mp 135° C.; IR (CDCl$_3$) 3065, 3030, 2947, 1756, 1656, 1213, 1065, 700 cm$^{-1}$; $^1$H NMR (300 MHz, CDCl$_3$) δ8.10 (d, J=7.14 Hz, 2H), 7.50 (m, 3H), 7.27 (m, 5H), 5.74, (d, J=10.8 Hz, 1H), 5.38 (d, J=10.8 Hz, 1H), 3.20 (s, 3H); $^{13}$C NMR (75 MHz, CDCl$_3$) δ168.3, 164.6, 136.8, 131.8, 128.6, 128.4, 128.3, 128.0, 127.9, 127.6, 126.6, 80.9, 73.4, 51.4; HRMS (FAB): Calcd for (M+H) C$_{17}$H$_{16}$NO$_3$, 282.1130; Found, 282.1134; EA Calcd for C$_{17}$H$_{15}$NO$_3$: C, 72.57; H, 5.38; N, 4.98; Found: C, 72.67; H, 5.44; N, 4.94.

Synthesis of Methyl (4S,5R)-2,4-diphenyl-4,5-dihydro-oxazole-5-carboxylate (or 2,4-Diphenyl-4(S),5(R)-dihydro-oxazole-5-carboxylic acid methyl ester) (3)

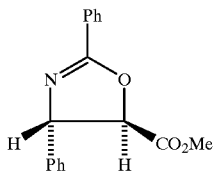

A 15 mL three-necked flask was charged with 2 (69 mg, 0.24 mmol) and dry THF (1.3 mL). The colorless solution was cooled to −50° C. and lithium bis(trimethylsilyl)amide (0.25 mL, 1 M solution in THF, 0.25 mmol) was added. The mixture was stirred for 10 minutes during which time a bright yellow color developed. The mixture was cooled to −78° C. and quenched with saturated NH$_4$Cl solution (0.5 mL). The mixture was diluted with ethyl acetate and water. The aqueous layer was extracted with ethyl acetate (3×). The combined organic layers were washed with brine, dried over MgSO$_4$, filtered, and evaporated to yield 69 mg (100%) of a mixture of 3 and 2. Crude $^1$H NMR indicated a 2:1 ratio of 3 to 2 respectively. The spectral data obtained for 3 was consistent with previously published data. IR 3065, 3030, 2952, 1756–1735, 1656, 1452, 1069, 695 cm$^{-1}$; $^1$H NMR (300 MHz, CDCl$_3$) δ8.10 (d, J=7.0 Hz, 2H),7.43 (m, 8H), 5.45 (d, J=6.4 Hz, 1H), 4.93 (d, J=6.4 Hz, 1H),3.87 (s, 3H); HRMS (FAB): Calcd. for (M+Li) C$_{17}$H$_{15}$NO$_3$Li, 288.1212; Found, 288.1222.

Synthesis tert-Butyl (4S,5R)-2,4-diphenyl-4,5-dihydro-oxazole-5-carboxylate (4)

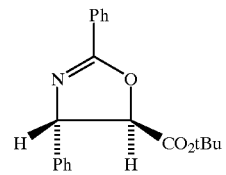

A 25 mL three-necked flask was charged with 2 (51.9 mg, 0.18 mmol) and dry THF (1.0 mL). The solution was cooled to 0° C. and lithium tert-butoxide (0.22 mL, 1.0 M solution in THF, 0.22 mmol) was added. After stirring for 10 minutes, the ice bath was removed and the reaction warmed to 25° C. The reaction mixture was then diluted with ethyl acetate and water. The aqueous layer was extracted with ethyl acetate (3×). The combined organic layers were washed with brine, dried over MgSO$_4$, filtered and evaporated to yield 45 mg (77%) of crude 4 which was contaminated with a trace of 2 and 3. Purification by silica gel column chromatography yielded pure 4 which was consistent with previously reported spectral data for the enantiomer of this compound. $^1$H NMR (300 MHz, CDCl$_3$) δ8.10 (d, J=7.2 Hz, 2H), 7.41 (m, 8H), 5.38 (d, J=6.5 Hz, 1H), 4.79 (d, J=6.5 Hz, 1H), 1.55 (s, 9H).

Esterification of Isopropanol-Synthesis of (4S,5R)-2,4-Diphenyl-4,5-dihydro-oxazole-5-carboxylic acid isopropyl ester (5)

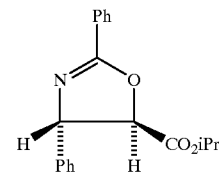

A 15 mL three-necked flask was charged with 2 (52.9 mg, 0.19 mmol) and dry THF (0.95 mL). The colorless solution was cooled to −50° C. After 15 minutes, lithium hexamethyldisilazide (0.22 mL, 1.0 M solution in THF, 0.22 mmol) was added and a bright yellow color developed. After 12 minutes, neat isopropanol (0.5 mL) was added and the reaction mixture was warmed gradually to 25° C. over one hour. The reaction mixture was diluted with ethyl acetate and water. The aqueous layer was extracted with ethyl acetate (3×). The combined organic layers were dried over MgSO$_4$, filtered and evaporated to yield 40.4 mg (69%) of a mixture of 5a and 5b. The ratio of 5b (trans) to 5a (cis) was determined to be 6:1 by crude $^1$H NMR. After purification by silica gel chromatography (5% ethyl acetate in hexanes) pure 5b was isolated as a clear oil which later became a white solid. R$_f$0.47 (4:1 hexanes/ethyl acetate); IR (CDCl$_3$) 2983, 2933, 1749, 1654, 1062 cm$^{-1}$; $^1$H NMR (300 MHz, CDCl$_3$) δ8.11 (m, 2H), 7.43 (m, 8H), 5.41 (d, J=6.6 Hz, 1H), 5.20 (m, 1H), 4.86 (d, J=6.6 Hz, 1H), 1.33 (m, 6H); $^{13}$C NMR (75 MHz, CDCl$_3$) δ169.6, 164.1, 141.2, 131.9, 128.8, 128.7, 128.4, 128.0, 126.8, 126.5, 83.2, 74.7, 69.6, 21.7;

HRMS (FAB): Calcd for (M+Li) $C_{19}H_{19}NO_3Li$, 316.1525; Found, 316.1519.

Using the procedure described above, t-butanol and (2S)-hydroxy-3-methylbutane were esterified as well.

Synthesis of tert-Butyl-(2S,3S,αS)-3-[N-benzyl-N-(α-methylbenzyl)amino]-2-hydroxy-3-phenyl propionate (6)

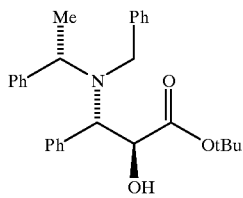

Compound 6 was prepared according to the literature procedure previously reported by Davies and co-workers (Bunnage et al., *J. Chem. Soc. Perkin Trans. I,* 1994, 2385). The spectral data below is consistent with the data for the enantiomer of 6 reported in the literature. IR (CDCl$_3$) 3495, 3023, 2977, 1724, 1494, 1454, 1369, 1112, 700 cm$^{-1}$; $^1$H NMR (300 MHz, CDCl$_3$) δ7.52 (d, J=7.5 Hz, 4H), 7.31 (m, 11H), 4.43 (bs, 1H), 4.25 (m, 2H), 4.16, 3.86 (ABq, J=15.0 Hz, 2H), 2.83 (bs, 1H), 1.24 (d, obscured, 3H), 1.23 (s, 9H); $^{13}$C NMR (75 MHz, CDCl$_3$) δ172.0, 144.0, 141.8, 138.2, 129.8, 128.2, 128.0, 127.95, 127.91, 127.5, 126.8, 126.6, 82.0, 73.3, 65.5, 57.2, 52.2, 27.6, 14.1; HRMS (FAB): Calcd for (M+Li) $C_{28}H_{33}NO_3Li$, 438.2620; Found, 438.2639.

Synthesis of tert-Butyl-(2S,3S,αS)-3-[N-benzyl-N-(α-methylbenzyl)amino]-2-benzoyl-oxy-3-phenylpropionate (7)

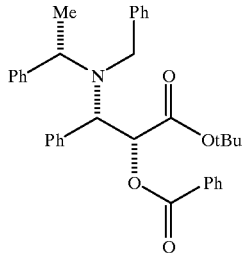

A 25 mL flask was charged with 6 (149.7 mg, 0.34 mmol). Dry triethylamine (0.1 mL, 0.71 mmol) and CH$_2$Cl$_2$ (1 mL) were added and the colorless solution was cooled to 0° C. Benzoyl chloride (40 μL, 0.34 mmol) was added and the reaction was gradually warmed to 25° C. After approximately 2 hours, 4-dimethylaminopyridine (49 mg, 0.40 mmol) was added along with an additional 40 μL of benzoyl chloride and 0.5 mL of CH$_2$Cl$_2$. (It was later discovered that 0.5 equivalents of DMAP and 1 equivalent of benzoyl chloride was sufficient to drive the reaction to completion in about 15 minutes.) After one hour the solvent was evaporated and the residue was partitioned between ether (6 mL) and water (6 mL). The mixture was extracted with ether (3x) and the organic layer was dried with MgSO$_4$, filtered, and evaporated. The crude product was a yellow oil contaminated with white crystals (benzoic acid) which were further precipitated with hexanes and filtered from the crude product. Purification of crude 7 by silica gel column chromatography (5% ethyl acetate in hexanes) yielded 148 mg (81%) of pure 7 as a clear oil. R$_f$0.60 (4:1 hexanes/ethyl acetate); IR (CDCl$_3$) 3024, 2977, 1727 broad, 1452, 1274, 1110, 700 cm$^{-1}$; $^1$H NMR (300 MHz, CDCl$_3$) δ8.04 (d, J=7.3 Hz, 2H), 7.73 (d, J=7.3 Hz, 2H), 7.36 (m, 16H), 5.69 (d, J=3.9 Hz, 1H), 4.67 (d, J=3.9 Hz, 1H), 4.25 (q, J=6.7 Hz, 1H), 4.02 (m, 2H), 1.29 (d, J=6.7 Hz, 3H), 1.22 (s, 9H); $^{13}$C NMR (75 MHz, CDCl$_3$) δ167.5, 165.5, 143.9, 141.5, 138.2, 132.9, 129.8, 129.7, 129.6, 128.2, 128.1, 128.0, 127.9, 127.7, 127.6, 126.9, 126.3, 81.9, 73.6, 63.9, 58.4, 52.2, 27.5, 15.9; HRMS (FAB): Calcd for (M+Li) $C_{35}H_{37}NO_4Li$, 542.2883; Found, 542.2902.

Synthesis of (2S,3S,αS)-3-[N-Benzyl-N-(α-methylbenzyl)amino]-2-benzoyl-oxy-3-phenyl-propionic acid (8)

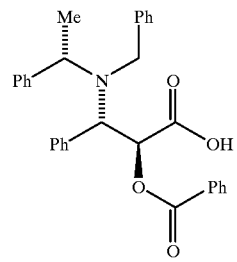

A 100 mL flask was charged with 7 (137 mg, 0.25 mmol) and dry CH$_2$Cl$_2$ (2.5 mL). Trifluoroacetic acid (0.8 mL) was added and the colorless solution was stirred at 25° C. for 3.5 hours. The reaction was quenched with several milliliters of a saturated NaHCO$_3$ solution and extracted with CH$_2$Cl$_2$ (3x). The organic layer was dried over MgSO$_4$, filtered, and evaporated. Purification by silica gel chromatography (4:1 hexanes/ethyl acetate increased to 1:1 hexanes/ethyl acetate) yielded 82 mg (68%) of 7 as a pure white foam. R$_f$ 0.06 (4:1 hexanes/ethyl acetate); IR (CDCl$_3$) 3031, 2930, 1726, 1269, 1113 cm$^{-1}$; $^1$H NMR (300 MHz, CDCl$_3$) δ12.63 (bs, 1H), 7.71 (d, J=7.4 Hz, 2H), 7.38 (m, 18H), 5.97 (d, J=9.8Hz, 1H), 4.88 (d, J=9.8 Hz, 1H), 4.34 (m, 2H), 3.90 (d, 13.8 Hz, 1H), 1.37 (d, J=6.8 Hz, 3H); $^{13}$C NMR (75 MHz, CDCl$_3$) δ171.0, 165.2, 138.0, 134.1, 133.1, 132.6, 129.7, 129.6, 129.4, 129.1, 129.0, 128.9, 128.5, 128.4, 128.1, 68.4, 62.8, 60.1, 51.8, 14.7.

Synthesis of Methyl-(2S,3S,αS)-3-[N-benzyl-N-(α-methylbenzyl)amino]-2-benzoyl-oxy-3-phenylpropionate (9)

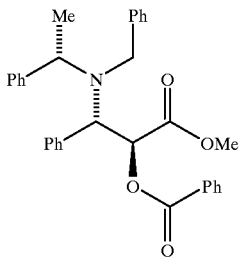

A 10 mL flask was charged with a 40% aqueous potassium hydroxide solution (0.9 mL) and dry ether (2 mL). While stirring with a teflon stirbar, nitrosomethyl urea (NMU) (103 mg, 1 mmol) was added. After stirring for 10 minutes open to the atmosphere, the yellow ether layer containing diazomethane was pipetted into a vial charged with one KOH pellet as a desiccant. A separate flask was charged with 8 (82 mg, 0.17 mmol) and dry ether (1 mL). After 30 minutes, the diazomethane ether solution was carefully pipetted into the clear solution of 8. The clear reaction mixture stirred for 20 minutes at 25° C. open to the atmosphere. The reaction was monitored by TLC (4:1 hexanes/ethyl acetate) and had not gone to completion. Therefore, another identical batch of diazomethane was prepared exactly as described above and added dropwise to the clear reaction mixture until a yellow color persisted, indicating that the reaction was complete. The reaction mixture and any remaining excess diazomethane were quenched with acetic acid (2 drops for the reaction mixture). The reaction mixture was extracted with ether (2×). The ether layer was dried over $MgSO_4$, filtered and evaporated to yield 71.6 mg (85%) of pure 9 as a white solid. $R_f$ 0.47 (4:1 hexanes/ethyl acetate); IR ($CDCl_3$) 3064, 3028, 2952, 1752, 1724, 1276, 1116, 904, 736 $cm^{-1}$; $^1H$ NMR (300 MHz, $CDCl_3$) δ7.80 (d, J=7.7 Hz, 2H), 7.36 (m, 18H), 5.67 (d, J=6.2 Hz, 1H), 4.60 (d, J=6.2 Hz, 1H), 4.18 (q, J=6.7 Hz, 1H), 4.06, 3.85 (ABq, J=14.5 Hz, 2H), 3.56 (s, 3H), 1.19 (d, J=6.8 Hz, 3H); $^{13}C$ NMR (75 MHz, $CDCl_3$) δ169.2, 165.4, 143.6, 140.4, 137.9, 133.1, 129.7, 129.3, 128.3, 128.2, 128.1, 127.9, 127.8, 126.9, 126.7, 73.2, 63.8, 57.2, 52.1, 51.9, 14.3; HRMS (FAB): Calcd for (M+Li) $C_{32}H_{31}NO_4Li$, 500.2413; Found, 500.2426.

Synthesis of (2S,3S,αS)-3-[N-benzyl-N-(α-methylbenzyl)amino]-2-benzoyl-oxy-3-phenyl-propionic anhydride (10)

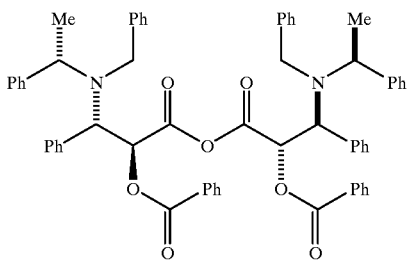

A 15 mL three-necked flask was charged with p-toluenesulfonyl chloride (28.5 mg, 0.15 mmol) and benzene (0.5 mL). A solution of 8 (73.3 mg, 0.15 mmol) in dry benzene (2 mL) was added to this clear solution. After stirring for 15 minutes, triethylamine (13.9 μl, 0.10 mmol) was added. TLC and IR indicated the presence of a new "anhydride" species although 8 was still present. Over a two hour period, additional triethylamine (47 μl) was added in an attempt to drive the reaction toward anhydride and ketene formation. The reaction mixture was then heated to gentle reflux for several hours and additional triethylamine (54 μl) was added before the mixture stirred overnight at 25° C. The reaction mixture was then evaporated and purified by column chromatography (9:1 hexane/ethyl acetate increased to 4:1 hexane/ethyl acetate) to yield 21.8 mg (15%) of pure 10 as an oil. Identification of 10 was confirmed by the fact that upon exposure of 10 to methanol, acid 8 and methyl ester 9 were isolated. Compounds 8 and 9 had been previously fully characterized. $R_f$ 0.42 (4:1 hexanes/ethyl acetate); IR 3063, 3030, 2972, 1833, 1728, 1273, 701 $cm^{-1}$; $^1H$ NMR (300 MHz, $CDCl_3$) δ7.80 (m, 4H), 7.30 (m, 36H), 5.45 (d, 2H), 4.57 (d, 2H), 4.10 (m, 2H), 3.90 (d, 2H), 3.70 (d, 2H), 1.16 (d, 6H).

Synthesis of 2-Benzoyloxy-3-phenyl-propionic Acid (11)

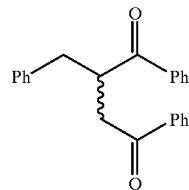

A 50 mL three-necked flask was charged with 3-phenyllactic acid (1.0 g, 6.0 mmol) and dry $CH_2Cl_2$ (12 mL). To this white slurry was added benzoyl chloride (1.04 mL, 9.0 mmol) and the mixture was cooled to 0° C. Triethylamine (0.8 mL, 6.0 mmol) was added and a light yellow solution resulted. 4-Dimethylaminopyridine (367 mg, 3.0 mmol) was added and the reaction mixture was warmed to 25° C. and stirred for 3 hours. The reaction mixture was concentrated on a rotary evaporator and ether, ethyl acetate, and water were added. The mixture was extracted with ether (3×) and ethyl acetate, dried over $MgSO_4$, filtered and evaporated. Purification by silica gel chromatography (4:1 hexanes/ethyl acetate increased to 1:1 hexanes/ethyl acetate) yielded 392 mg (24%) of 11 as a white solid. $R_f$ 0.15 (1:1 hexanes/ethyl acetate); mp 113° C.; IR ($CDCl_3$) 3564–2560 (broad acid), 3028, 2924, 1720 (broad), 1452, 1268, 716 $cm^{-1}$; $^1H$ NMR (300 MHz, $CDCl_3$) δ11.25 (s, 1H), 8.08 (d, J=7.2 Hz, 2H) 7.45 (m, 8H), 5.56 (m, 1H), 3.38 (m, 2H); $^{13}C$ NMR (75 MHz, $CDCl_3$) δ175.5, 165.9, 149.9, 135.6, 133.4, 130.1, 129.7, 129.3, 128.9, 128.5, 128.4, 127.1, 72.9, 37.2; HRMS (FAB): Calcd for (M+Li) $C_{16}H_{14}O_4Li$, 277.1052; Found, 277.1065; EA Calcd for $C_{16}H_{14}O_4$: C, 71.10; H, 5.22; Found: C, 71.04; H, 5.24.

1,4-Dimethyl-5,8-dioxo-1,5,8,8a-tetrahydro-4H-naphthalene-4a-carboxylic acid methyl ester (12)

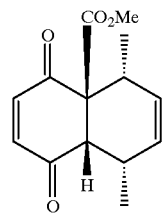

1.7 g (10 mmol) of 2,5-dihydroxymethylbenzoate was stirred with 0.9 g (11 mmol) of 2,3-hexadiene in 20 ml of benzene at 10° C. 4.62 g (20 mmol) of $Ag_2O$ was added to the reaction mixture. Cooling bath was removed and the reaction mixture was stirred overnight in darkness. The reaction mixture was deluded with 100 ml of $Et_2O$, filtered through 1 inch silica gel plug and concentrated to yield 2.3 g (93%) of 12 as an orange solid. $^1H$ NMR (300 MHz, $C_6H_6$): δ1.06 (m, 6H), 2.32 (m, 1H), 2.88 (q, 1H), 3.24 (s, 3H), 3.64 (d, 1H),5.39 (s, 2H), 6.13 (q, 2H); $^{13}C$ NMR (75 MHz, $CDCl_3$): δ17.2, 17.8, 30.1, 34.4, 53.3, 53.5, 63.1, 128.2, 128.6, 141.8, 142.5, 171.5, 196.7, 198.1; IR (neat): 750.5, 918.8, 1259.6, 1467.7, 1680.2, 1715.6, 1746.6, 3114.6 $cm^{-1}$; HRMS calculated for $C_{14}H_{16}O_4+H^+$: 249.1127, found: 249.1131.

1,4-Dimethyl-5,8-dioxo-1,5,8,8a-tetrahydro-4H-naphthalene-4a-carboxylic acid methyl ester (13)

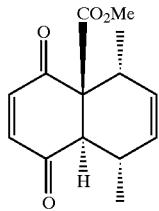

2.5 g (10 mmol) of 12 was dissolved in 20 ml of toluene. 1.25 g (11 mmol) of DABCO was added and the reaction mixture was stirred for 14 hours at room temperature. The reaction mixture was deluded with 100 ml of $Et_2O$, filtered through 1 inch silica gel plug and concentrated to yield 2.4 g (93%) of 13 as an orange solid. $^1H$ NMR (300 MHz, $CDCl_3$): δ0.96 (d, 3H, J=6.9 Hz), 1.16 (m, 3H), 2.88 (m, 1H), 3.24 (q, 1H), 3.64 (s, 4H), 5.39 (dd, 1H), 5.64 (m, 1H), 6.58 (d, 1H), 6.80 (d, 1H); $^{13}C$ NMR (75 MHz, $CDCl_3$): δ17.2, 17.8, 30.1, 34.4, 53.3, 53.5, 63.1, 128.2, 128.6, 141.8, 142.5, 171.5, 196.7, 198.1; IR (neat): 750.4, 918.9, 1259.7, 1467.7, 1680.1, 1715.4, 1746.7, 3114.5 $cm^{-1}$; HRMS calculated for $C_{14}H_{16}O_4+H^+$: 249.112, found: 249.114.

1,4-Dimethyl-5,8-methano-9,10-dioxo-1,5,8,8a,9,9a10,10a-octahydro-4H-antracene-4a-carboxylic acid methyl ester (14)

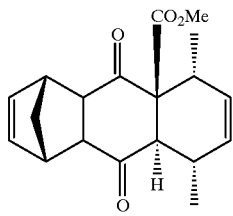

0.5 g (2 mmol) of 13 was stirred with 1.3 g (20 mmol) of freshly distilled cyclopentadiene in 20 ml of EtOH at room temperature for 10 hours. The reaction mixture was concentrated on rotavap to yield. 57 g (91%) of 14 as a white solid. $^1H$ NMR (300 MHz, $CDCl_3$): δ0.86 (d, 3H, J=6.9 Hz), 1.03 (d, 3H, J=7.0 Hz), 1.37 (d, 1H), 1.45 (d, 1H), 2.08 (d, 1H), 2.73 (m, 1H), 3.11 (m, 2H), 3.24 (m, 1H), 3.39 (s, 1H), 3.59 (s, 4H), 5.32 (dd, 1H), 5.62 (m, 1H), 6.16 (m, 1H), 6.22 (m, 1H); $^{13}C$ NMR (75 MHz, $CDCl_3$): δ17.85, 22.29, 30.49, 32.79, 49.12, 49.64, 49.83, 50.38, 50.55, 52.49, 53.27, 67.45, 129.49, 131.46, 135.60, 137.74, 169.77, 203.95, 208.66; IR ($CDCl_3$): 732.4, 914.9, 1214.9, 1247.3, 1470.4, 1705.5, 1750.1, 2982.4 $cm^{-1}$; HRMS calculated for $C_{19}H_{22}O_4+H^+$: 315.159, found: 315.160.

9-Hydroxy-1,4-dimethyl-5,8-methano-10-oxo-1,5,8,8a,9,9a,10,10a-octahydro-4H-anthracene-4a-carboxylic acid methyl ester (15)

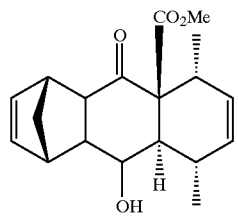

0.96 g (3 mmol) of 14 was dissolved in 5 ml of anhydrous THF and cooled to −78° C. 0.8 ml of LAH (1M, THF) was added. After 2 hours TLC indicated no 14 was left. The reaction mixture was quenched with 2 g of solid $NH_4Cl$ and deluded with 50 ml of ether. The reaction mixture was washed with 10% HCl, twice with water, dried over magnesium sulfate and concentrated. Silica gel column (Hexanes:EtOAc, 4:1) yielded 0.62 g (65%) of 17. $^1H$ NMR (300 MHz, $CDCl_3$): δ0.82 (d, 3H, J=6.9 Hz), 1.23 (d, 3H, J=7.0 Hz), 1.28 (m, 2H), 1.37 (d, 1H, J=8 Hz), 1.62 (br.s, 1H) 1.78 (dd, 1H, J=8 Hz, J=3.1 Hz), 2.47 (br.m, 1H), 2.96 (m, 2H), 3.21 (s, 1H), 3.44 (m, 1H), 3.59 (s, 3H), 4.88 (br.t, 1H, J=9.2), 5.38 (dd, 1H, J=7.1 Hz, J=3.1 Hz), 5.61 (m, 1H), 6.08 (m, 1H), 6.21 (m, 1H); $^{13}C$ NMR (75 MHz, $CDCl_3$): δ17.55, 23.53, 34.67, 35.55, 40.24, 44.06, 45.65, 48.85, 49.50, 51.63, 52.44, 71.86, 128.49, 133.42, 135.73, 137.28, 169.97, 207.56; IR ($CDCl_3$): 732.4, 914.9, 1214.9, 1247.3, 1470.4, 1705.5, 1750.1, 2982.4, 3544.3 $cm^{-1}$; HRMS calculated for $C_{19}H_{24}O_4+H^+$: 323.1758, found: 323.1775.

9-Benzoyloxy-1,4-dimethyl-5,8-methano-10-oxo-1,5,8,8a,9,9a,10,10a-octahydro-4H-anthracene-4a-carboxylic acid methyl ester (16)

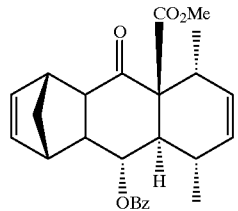

0.15 g (0.45 mmol) of 15 was dissolved in 9 ml of 1:1:1 mixture of anhydrous $CH_2Cl_2$, triethylamine and anhydrous DMF. 0.2 ml of benzoyl chloride was added followed by catalytic amount of DMAP (0.01 g). In 24 hours the reaction mixture was quenched by pouring into 50 ml of 1:1 mixture of water and ether. The organic layer was washed with water, twice with saturated solution of ammonium chloride and with $NaHCO_3$. Ether solution was dried over magnesium sulfate and concentrated. Silica gel column (Hexanes:EtOAc, 3:1) yielded 0.12 g (78%) of 16. $^1H$ NMR (300 MHz, $CDCl_3$): δ0.82 (d, 3H, J=6.9 Hz), 1.13 (d, 3H, J=7.0 Hz), 1.23 (m, 2H), 2.16 (d, 1H, J=2.8 Hz), 2.37 (br.m, 1H,), 2.86 (s, 1H), 3.01 (dd, 1H, J=3.2 Hz, J=5 Hz), 3.11 (m, 1H), 3.35 (m, 1H), 3.42 (s, 1H), 3.61 (s, 3H), 5.28 (dd, 1H, J=7.1 Hz, J=3.1 Hz), 5.61 (m, 1H), 6.12 (m, 1H), 6.22 (t, 1H, J=9.2), 6.31 (m, 1H), 7.43–8.07 (m, 5H); $^{13}C$ NMR (75 MHz, $CDCl_3$): δ17.44, 22.93, 34.30, 35.88, 40.80, 46.83, 48.84, 48.88, 51.50, 52.74, 64.51, 75.83, 128.39, 128.65, 128.92, 129.66, 129.71, 130.19, 132.86, 133.18, 133.58, 135.83, 137.33, 166.71, 169.97, 207.35; IR (neat): 732.4, 914.9, 1214.9, 1247.3, 1470.4, 1705.5, 1712.2, 1750.1, 2982.4 cm$^{-1}$; HRMS calculated for $C_{26}H_{28}O_5$+H$^+$: 421.1251, found: 421.1246.

9-Benzoyloxy-1,4-Dimethyl-6-hydroxy-5,8-methano-10-oxo-1,5,6,7,8,8a,9,9a10,10a-decahydro-4H-antracene-4a-carboxylic acid methyl ester (17) and 9-Benzoyloxy-1,4-Dimethyl-7-hydroxy-5,8-methano-10-oxo-1,5,6,7,8,8a,9,9a,10,10a-decahydro-4H-antracene-4a-carboxylic acid methyl ester (18)

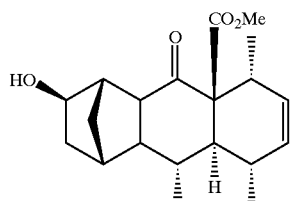

17

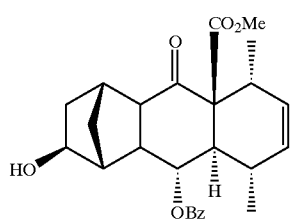

18

0.42 g (1 mmol) of 16 was dissolved in 20 ml of anhydrous THF. 1.5 ml of BH$_3$*SMe$_2$ (2M, in THF, 3 eq.) was added to the solution at 0° C. The reaction mixture was stirred for 2 hours at 0° C. until TLC indicated the complete consumption of 16. After that the reaction mixture was deluded with 10 ml of MeOH. 0.1 g of NaOAc was added to the solution as a solid. Finally, 2 ml of 30% H$_2$O$_2$ was added. After two hours the reaction mixture was filtered through 1 inch silica gel plug, dried over magnesium sulfate and concentrated. Silica gel column yielded 0.44 g (82%) of 2:1 mixture of alcohols 17 and 18. 17: $^1$H NMR (300 MHz, CDCl$_3$): δ0.96 (d, 3H, J=6.9 Hz), 1.13 (d, 3H, J=7.0 Hz), 1.22 (m, 2H), 1.57 (d, 1H, J=9.1 Hz), 1.83 (m, 2H), 2.12 (m, 2H), 2.43 (br.m, 1H), 2.62 (m, 1H), 2.86 (m, 1H), 3.04 (m, 1H), 3.15 (m, 1H), 3.61 (s, 3H), 3.78 (d, 1H, J=3 Hz), 5.38 (dd, 1H, J=7.1 Hz, J=3.1 Hz), 5.61 (t, 1H, J=3.1 Hz), 6.29 (t, 1H, J=9.4 Hz), 7.43–8.07 (m, 5H); $^{13}$C NMR (75 MHz, CDCl$_3$): δ17.68, 22.62, 34.28, 34.67, 40.41, 47.72, 48.47, 49.65, 50.84, 52.83, 64.81, 75.35, 128.39, 128.65, 128.92, 129.66, 129.71, 130.19, 132.86, 133.18, 133.58, 135.83, 137.33, 165.92, 169.17, 207.28; IR (CDCl$_3$): 732.4, 914.9, 1214.9, 1247.3, 1470.4, 1705.5, 1712.2, 1750.1, 2982.4 cm$^{-1}$; HRMS calculated for $C_{26}H_{30}O_6$+Li$^+$: 445.2202, found: 445.2197. 18: $^1$H NMR (300 MHz, CDCl$_3$): δ0.94 (d, 3H, J=6.9 Hz), 1.15 (d, 3H, J=7.0 Hz), 1.23 (m, 2H), 1.62 (d, 1H, J=9.1 Hz), 1.81 (m, 2H), 2.16 (m, 2H), 2.43 (br.m, 1H), 2.62 (m, 1H), 2.86 (m, 1H), 3.04 (m, 1H), 3.18 (t, 1H, J=7.1 Hz), 3.61 (s, 3H), 4.38 (d, 1H, J=3 Hz), 5.28 (dd, 1H, J=7.1 Hz, J=3.1 Hz), 5.61 (m, 1H), 6.22 (t, 1H, J=9.4 Hz), 7.43–8.07 (m, 5H); $^{13}$C NMR (75 MHz, CDCl$_3$): δ17.44, 22.93, 34.30, 35.88, 40.80, 46.83, 48.84, 48.88, 51.50, 52.74, 64.51, 75.83, 128.39, 128.65, 128.92, 129.66, 129.71, 130.19, 132.86, 133.18, 133.58, 135.83, 137.33, 166.71, 169.97, 207.35; IR (CDCl$_3$): 732.4, 914.9, 1214.9, 1247.3, 1470.4, 1705.5, 1712.2, 1750.1, 2982.4 cm$^{-1}$; HRMS calculated for $C_{26}H_{30}O_6$+Li$^+$: 445.2202, found: 445.2197.

9-Benzoyloxy-1,4-Dimethyl-5,8-methano-6,10-dioxo-1,5,6,7,8,8a,9,9a10,10a-decahydro-4H-antracene-4a-carboxylic acid methyl ester (19)

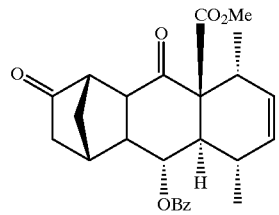

0.44 g (1 mmol) of 17 was dissolved in 10 ml of dicloromethane and 0.22 g (1.1 eq) of PCC was added. After stirring for 6 hours at room temperature TLC indicated that no 17 was left. The reaction mixture was filtered through 1 inch silica gel plug, dried over magnesium sulfate and concentrated. Silica gel gravity column (Hexanes:EtOAc, 4:1) yielded 0.36 g (68%) of 19 as a white foam. $^1$H NMR (300 MHz, CDCl$_3$): δ0.84 (d, 3H, J=6.9 Hz), 1.15 (d, 3H, J=7.0 Hz), 1.23 (m, 2H), 1.62 (d, 1H, J=9.1 Hz), 2.16 (m, 3H), 2.43 (br.m, 2H), 2.62 (m, 1H), 3.09 (m, 4H), 3.42 (t, 1H, J=7.1 Hz), 3.61 (s, 3H), 5.28 (dd, 1H, J=7.1 Hz, J=3.1 Hz), 5.61 (m, 1H), 6.32 (t, 1H, J=9.8 Hz), 7.43–8.07 (m, 5H); $^{13}$C NMR (75 MHz, CDCl$_3$): δ17.58, 22.93, 34.16, 36.32, 39.73, 40.86, 47.83, 52.91, 54.76, 64.78, 74.73, 128.75, 129.06, 129.71, 132.19, 133.86, 135.83, 147.33, 166.71, 169.97, 203.35, 213.28; IR (CDCl$_3$): 732.4, 1064.1, 1111.3, 1274.9, 1446.5.4, 1446.5, 1712.5, 1743.1, 2847.3, 2924.4 cm$^{-1}$; HRMS calculated for $C_{26}H_{28}O_6$+Li$^+$: 445.2202, found: 445.2197.

9-Benzoyloxy-1,4-Dimethyl-6-hydroxy-5,8-methano-10-oxo-1,5,6,7,8,8a,9,9a,10,10a-decahydro-4H-antracene-4a-carboxylic add methyl ester (20)

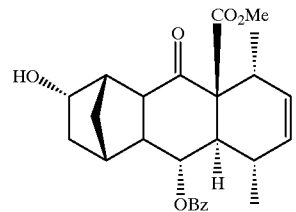

0.44 g (1 mmol) of 19 was dissolved in 20 ml of anhydrous toluene and 1.1 ml of lithium tritertbutoxyaluminun hydride (1M, THF) was added at 0° C. The reaction mixture was stirred for 20 hours then was quenched with 3 ml of saturated solution of ammonium chloride and deluded with 20 ml of ether. The reaction mixture was washed with water, dried over magnesium sulfate and concentrated. Preparative TLC yielded 0.41 g (86%) of 20 as colorless oil. $^1$H NMR (300 MHz, CDCl$_3$): δ1.06 (d, 3H, J=6.9 Hz), 1.17 (d, 3H, J=7.0 Hz), 1.44 (m, 2H), 1.89 (m, 1H), 2.08 (dd, 2H, J=3.0 Hz, J=5.2 Hz), 2.31 (m, 1H), 2.39 (dd, 1H, J=9.8 Hz, J=3.8 Hz), 2.81 (m, 1H), 3.08 (m 2H), 3.18 (m, 1H), 3.58 (m, 1H), 3.71 (s, 3H), 4.60 (m, 1H), 5.38 (m, 1H), 5.64 (m, 1H), 1H, J=9.8 Hz, J=3.8 Hz), 7.34–8.08 (m, 5H); $^{13}$C NMR (75 MHz, CDCl$_3$): δ19.14, 23.05, 34.34, 36.18, 37.15, 37.46, 37.88, 40.44, 41.04, 46.73, 48.53, 52.44, 57.02, 78.10, 80.97, 126.27, 128.38, 128.42, 128.54, 129.24, 129.60, 130.13, 132.63, 133.01, 166.09, 171.05, 176.39, 205.66; IR (neat): 732.4, 1064.1, 1111.3, 1274.9, 1446.4, 1446.5, 1712.5, 1743.1, 2847.3, 2924.4 cm$^{-1}$; HRMS calculated for $C_{26}H_{30}O_6+Li^{30}$: 445.2202, found: 445.2197.

1,4-Dimethyl-7-hydroxy-5,8-methano-9,10-dioxo-1,
5,6,7,8,8a,9,9a,10,10a-decahydro-4H-antracene-4a-
carboxylic add methyl ester (21), 1,4-Dimethyl-6-
hydroxy-5,8-methano-9,10-dioxo-1,5,6,7,8,8a,9,9a,
10,10a-decahydro-4H-antracene-4a-carboxylic acid
methyl ester (22) and 1,4-Dimethyl-5,8-methano-9,
10-dioxo-1,5,6,7,8,8a,9,9a,10,10a-decahydro-4H-
antracene-4a-carboxylic acid methyl ester (23)

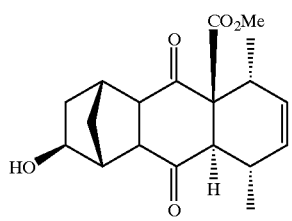

21

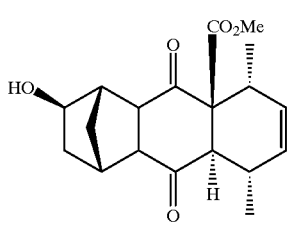

22

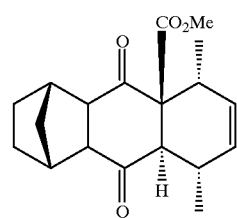

23

I. Catalytic Hydroboration 0.48 g (1.5 mmol) of 20 was dissolved in 20 ml of anhydrous THF. 0.01 g of Wilkinson's catalyst was added to the solution at 0° C. After 20 min. 0.25 ml of $H_3*SMe_2$ (2M, in THF) was added dropwise. Cooling bath was removed and the reaction mixture was stirred at 23° C. overnight. After 24 hours the reaction mixture was deluded with 10 ml of MeOH. 2.5 ml of NaOH (3N) was added followed by 0.35 ml of 30% $H_2O_2$. After additional hour the reaction mixture was filtered through 1 inch silica gel plug, dried over magnesium sulfate and concentrated. Silica gel column yielded 0.37 g (70%) of 20 and 0.09 g (18%) of 2:1 mixture of alcohols 21 and 22.

II. Hydroboration with excess of $BH_3*SMe_2$ 0.48 g (1.5 mmol) of 20 was dissolved in 20 ml of anhydrous THF at 0° C. 2.25 ml of $BH_3*SMe_2$ (2M, in THF, 3 eq.) was added to the solution. Reaction was stirred for 2 hours at 0° C. until TLC indicated the complete consumption of 20. After that the reaction mixture was deluded with 10 ml of MeOH. 2.5 ml of NaOH (3N) was added followed by 3 ml of 30% $H_2O_2$. After additional hour the reaction mixture was filtered through 1 inch silica gel plug, dried over magnesium sulfate and concentrated. Silica gel column yielded 0.44 g (82%) of 2:1 mixture of alcohols 21 and 22 and 0.04 g (7%) of 23. 21: $^1$H NMR (300 MHz, $CDCl_3$): δ0.86 (d, 3H, J=6.9 Hz), 1.15 (d, 3H, J=7.0 Hz), 1.37 (m, 2H), 1.77 (m, 1H), 2.08 (d, 2H), 2.73 (m, 1H), 2.79 (m, 3H), 2.91 (m, 1H), 3.08 (m, 1H), 3.18 (q, 1H), 3.59 (s, 3H), 3.79 (d, 1H), 5.38 (m, 1H), 5.69 (m, 1H); $^{13}$C NMR (75 MHz, $CDCl_3$): δ17.85, 23.29, 30.49, 32.79, 34.15, 37.55, 42.55, 49.12, 49.64, 50.38, 52.49, 53.27, 67.45, 69.55, 128.49, 131.46, 169.77, 203.95, 208.66; IR ($CDCl_3$): 744.4, 918.9, 1213.9, 1280.3, 1376.4, 1464.1, 1700.5, 1727.1, 2923.4 cm$^{-1}$; HRMS calculated for $C_{19}H_{22}O_4+Li^+$: 339.1784, found: 339.1780. 22: $^1$H NMR (300 MHz, $CDCl_3$): δ0.88 (d, 3H, J=6.9 Hz), 1.11 (d, 3H, J=7.0 Hz), 1.33 (m, 2H), 1.79 (m, 1H), 2.08 (d, 2H), 2.71 (m, 1H), 2.79 (m, 3H), 2.93 (m, 1H), 3.08 (m, 1H), 3.18 (q, 1H), 3.59 (s, 3H), 3.72 (d, 1H, J=3.2 Hz), 5.38 (m, 1H), 5.69 (m, 1H); $^{13}$C NMR (75 MHz, $CDCl_3$): δ17.85, 23.24, 30.43, 32.79, 34.15, 37.54, 42.55, 49.22, 49.64, 50.38, 52.49, 53.27, 66.45, 69.32, 128.45, 131.43, 169.77, 203.91, 208.71; IR ($CDCl_3$): 744.4, 918.9, 1213.9, 1280.3, 1376.4, 1464.1, 1700.5, 1727.1, 2923.4 cm$^{-1}$; HRMS calculated for $C_{19}H_{22}O_4+Li^+$: 339.1784, found: 339.1780. 23: $^1$H NMR (300 MHz, $CDCl_3$): δ0.96 (d, 3H, J=6.9 Hz), 1.13 (d, 3H, J=7.0 Hz), 1.21–1.57 (m, 4H), 2.22 (d, 1H), 2.73–3.08 (m, 4H), 3.22 (m, 1H), 3.57 (s, 3H), 5.38 (dd, 1H), 5.68 (m, 1H); $^{13}$C NMR (75 MHz, $CDCl_3$): δ17.93, 22.57, 24.67, 25.04, 30.77, 32.68, 39.01, 42.40, 43.49, 49.58, 50.23, 50.99, 52.48, 53.08, 67.90, 129.17, 131.53, 169.52, 205.07, 209.43; IR (neat): 733.8, 914.3, 1216.5, 1248.1, 1460.2, 1703.8, 1739.8, 2971.4 cm$^{-1}$; HRMS calculated for $C_{19}H_{24}O_4+H^+$: 317.1753, found: 317.1741.

1,4-Dimethyl-5,8-methano-7,9,10-trioxo-1,5,6,7,8,
8a,9,9a,10,10a-decahydro-4H-antracene-4a-
carboxylic acid methyl ester (24)

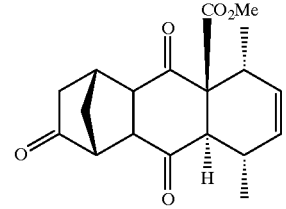

0.16 g (0.5 mmol) of 22 was dissolved in 10 ml of dichloromethane and 0.11 g (1.1 eq) of PCC was added. After stirring an for 6 hours at room temperature TLC indicated that no 21 was left. The reaction mixture was filtered through 1 inch silica gel plug, dried over magnesium sulfate and concentrated. Silica gel column (Hexanes:EtOAc, 4:1) yielded 0.12 g (73%) of 24 as a white foam. $^1$H NMR (300 MHz, $CDCl_3$): δ0.82 (d, 3H, J=6.9 Hz), 1.12 (d, 3H, J=7.0 Hz), 1.77 (m, 2H) 1.85 (m, 2H), 2.05 (m, 2H), 2.76 (m, 1H), 3.11 (m, 3H), 3.32 (m, 1H), 3.58 (s, 3H), 5.38 (m, 1H), 5.69 (m, 1H); $^{13}$C NMR (75 MHz, $CDCl_3$): δ17.68, 22.32, 30.75, 31.48, 32.46, 37.78, 41.43, 42.19, 49.68, 51.33, 53.26, 54.36, 67.47, 129.16, 130.92, 169.41, 200.71, 207.71, 212.73; IR ($CDCl_3$): 732.8, 915.6, 1075.0, 1154.7, 1220.3, 1248.4, 1464.1, 1712.5, 1750.0, 2954.7 cm$^{-1}$; HRMS calculated for $C_{19}H_{22}O_4+Li^+$: 337.1627, found: 337.1622.

1,4-Dimethyl-5,8-methano-6,9,10-trioxo-1,5,6,7,8, 8a,9,9a,10,10a-decahydro-4H-antracene-4a-carboxylic add methyl ester (25)

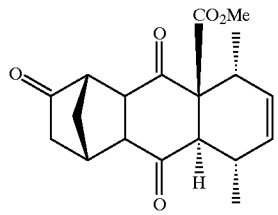

A solution of 85 mg (1.1 mmol) of freshly dried DMSO in 1 ml of anhydrous $CH_2Cl_2$ was added to a solution of 70 mg (0.55 mmol) of oxalyl chloride in 1.2 ml of anhydrous $CH_2C_2$, stirred and cooled to −78° C. After stirring an additional 5 min., a solution of 0.16 g (0.5 mmol) of 22 dissolved in 1 iA of was anhydrous $CH_2Cl_2$ added dropwise over 10 min. After stirring an additional 15 min. at −78° C., the reaction mixture was warmed up to −10° C. and 0.35 ml (2.5 mmol) of dried $Et_3N$ was added dropwise over 30 min. Finally, cooling bath was removed and the reaction mixture was warmed up to room temperature. After 45 min. 100 ml of EtOAc was added followed by 20 ml of water. Organic layer was separated, dried over magnesium sulfate and concentrated. Silica gel column (Hexanes:EtOAc, 4:1) yielded 0.12 g (73%) of 27 as a white foam. $^1$H NMR (300 MHz, $CDCl_3$): δ0.92 (d, 3H, J=6.9 Hz), 1.07 (d, 3H, J=7.0 Hz), 1.77 (m, 1H), 1.85 (m, 2H), 2.08 (m, 2H), 2.76 (m, 1H), 3.08 (m, 3H), 3.32 (q, 2H), 3.59 (s, 3H), 5.38 (dd, 1H), 5.69 (m, 1H); $^{13}$C NMR (75 MHz, $CDCl_3$): δ17.81, 21.98, 30.42, 32.47, 37.96, 40.69, 42.95, 49.15, 49.27, 50.50, 53.33, 67.45, 56.75, 68.03, 128.91, 131.16, 169.31, 204.11, 205.08, 212.63; IR (neat): 732.8, 915.6, 1075.0, 1154.7, 1220.3, 1248.4, 1464.1, 1712.5, 1750.0, 2954.7 cm$^{-1}$; HRMS calculated for $C_{19}H_{22}O_4+Li^+$: 337.1627, found: 337.1622.

1,4-Dimethyl-6-hydroxy-5,8-methano-9,10-dioxo-1, 5,6,7,8,8a,9,9a,10,10a-decahydro-4H-antracene-4a-carboxylic acid methyl ester (26)

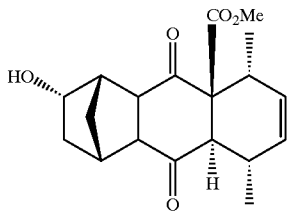

0.08 g of 25 (0.23 mmol) was dissolved in 5 ml of anhydrous THF and 0.25 ml of DIBAL-H (1M, Hexanes) was added at 0° C. the reaction mixture was stirred at room temperature for 20 hours then was quenched with 5 ml of 10% HCl and deluded with 20 ml of ether. the reaction mixture was washed with water, dried over magnesium sulfate and concentrated. Preparative TLC yielded 0.041 g (50%) of 26 as colorless oil. $^1$H NMR (300 MHz, $CDCl_3$): δ1.11 (m, 3H), 1.20 (m, 3H), 1.45 (m, 2H), 1.77 (m, 1H), 2.73 (m, 1H), 2.91 (m 4 2H), 3.08 (m, 1H), 3.22 (m, 2H), 3.39 (d, 1H), 3.62 (s, 3H), 4.42 (m, 1H), 5.42 (m, 1H), 5.72 (m, 1H); $^{13}$C NMR (75 MHz, $CDCl_3$): δ17.75, 23.29, 31.49, 32.79, 34.15, 37.55, 42.55, 48.12, 49.64, 50.38, 52.49, 53.27, 67.45, 73.55, 128.49, 133.46, 169.77, 205.00, 207.50; IR (neat): 744.4, 1100.9, 1228.3, 1249.6, 1382.4, 1461.9, 1700.9, 1727.1, 2923.4 cm$^1$; HRMS calculated for $C_{19}H_{22}O_4+H^+$: 333.1702, found: 333.1692.

Throughout this application, various publications are referenced. The disclosures of these publications in their entireties are hereby incorporated by reference into this application in order to more fully describe the state of the art to which this invention pertains.

Although the present methods and compounds have been described with reference to specific details of certain embodiments thereof, it is not intended that such details should be regarded as limitations upon the scope of the invention except as and to the extent that they are included in the accompanying claims.

What is claimed is:

1. A method for preparing a compound having the structure VII:

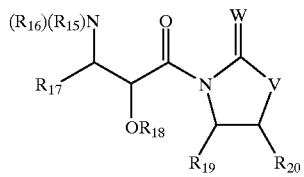

VII wherein, $R_{15}$ and $R_{16}$ are, independently, hydrogen, $Si(R_{21})_3$ or $C(O)R_{22}$, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is branched or straight chain $C_1$–$C_{12}$ alkyl; unsubstituted or substituted aryl; aralkyl; $Si(R_{28})_3$ or $C(O)R_{29}$, wherein, each $R_{28}$ is, independently, branched or straight chain $C_1$–$C_{12}$ alkyl; or aralkyl;

$R_{29}$ is substituted or unsubstituted aryl, aralkyl or from $C_1$–$C_{12}$ branched or straight chain alkyl;

$R_{19}$ and $R_{20}$ are, independently, branched or straight chain $C_1$–$C_{12}$ alkyl, aryl, aralkyl, or $C(O)OR_{30}$;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl, comprising, (a) admixing
 (i) a compound having the structure X

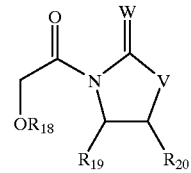

X wherein $R_{18}$–$R_{20}$ are as above,
 (ii) a Lewis acid; and
 (iii) a base,
to produce a first intermediate;

(b) reacting the first intermediate of step (a) with a compound having the structure XI:

XI wherein $R_{15}$ and $R_{17}$ are as above,
to produce a second intermediate; and
(c) admixing the second intermediate of step (b) with a proton source.

2. The method of claim 1, wherein the base comprises an amide, a secondary amine or a tertiary amine.

3. The method of claim 1, wherein a compound having the structure X is admixed with the Lewis acid prior to admixing the base.

4. The method of claim 1, wherein the Lewis acid comprises stannous triflate, stannic chloride, stannous chloride, dialkylboron triflate, or titanium tetrachloride.

5. The method of claim 1, wherein $R_{15}$ is C(O)Ph.

6. A compound having the structure VII:

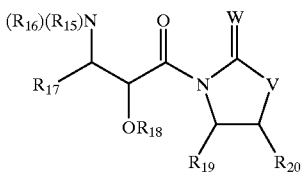

VII wherein, $R_{15}$ and $R_{16}$ are, independently, hydrogen, $Si(R_{21})_3$ or $C(O)R_{22}$, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is hydrogen; branched or straight chain $C_1$–$C_{12}$ alkyl; unsubstituted or substituted aryl; aralkyl; $Si(R_{28})_3$ or $C(O)R_{29}$, wherein, each $R_{28}$ is, independently, branched or straight chain $C_1$–$C_{12}$ alkyl; or aralkyl;

$R_{29}$ is substituted or unsubstituted aryl, aralkyl or from $C_1$–$C_{12}$ branched or straight chain alkyl;

$R_{19}$ and $R_{20}$ are, independently, branched or straight chain $C_1$–$C_{12}$ alkyl, aryl, aralkyl, or $C(O)OR_{30}$;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl.

7. The compound of claim 6, wherein V and W are sulfur.

8. The compound of claim 6, wherein $R_{17}$ is phenyl and $R_{18}$ is benzoyl.

9. The compound of claim 6, wherein $R_{18}$ is hydrogen.

10. The compound of claim 6, wherein $R_{16}$ is C(O)Ph.

11. The compound of claim 6, wherein $R_{16}$ is C(O)Ph and $R_{18}$ is hydrogen.

12. A method for preparing a compound having the structure VII:

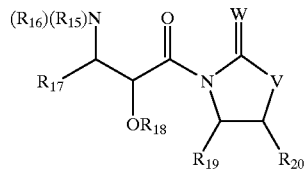

VII wherein, $R_{15}$ and $R_{16}$ are, independently, hydrogen, $Si(R_{21})_3$ or C(O)OMe, wherein each $R_{21}$ is, independently, branched or straight chain $C_1$–$C_{12}$ alkyl; and $R_{22}$ is substituted or unsubstituted aryl, aralkyl or from $C_1$–$C_{12}$ branched or straight chain alkyl;

$R_{17}$ is substituted or unsubstituted aryl, aralkyl, or from $C_1$–$C_{12}$ branched or straight chain alkyl;

$R_{18}$ is hydrogen:

$R_{19}$ and $R_{20}$ are, independently, branched or straight chain $C_1$–$C_{12}$ alkyl, aryl, aralkyl, or $C(O)OR_{30}$;

$R_{30}$ is branched or straight chain $C_1$–$C_{12}$ alkyl; and

V and W are, independently, sulfur, oxygen, or $NR_{43}$, wherein $R_{43}$ is hydrogen; branched or straight chain $C_1$–$C_{12}$ alkyl; or aralkyl, comprising,
(a) admixing
(i) a compound having the structure XIII

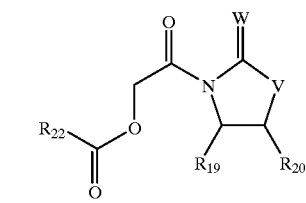

XIII wherein $R_{19}$–$R_{20}$ and $R_{22}$ are as above,
(ii) a Lewis acid; and
(iii) a first base,
to produce a first intermediate;
(b) reacting the first intermediate of step (a) with a compound having the structure XI:

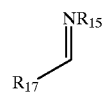

XI wherein $R_{15}$ and $R_{17}$ are as above,
to produce a second intermediate; and
(c) admixing the second intermediate with a basic buffer, wherein the buffer comprises a second base.

13. The method of claim 12, wherein the first base comprises an amide, a secondary amine or a tertiary amine.

14. The method of claim 12, wherein the compound having the structure XIII and the Lewis acid are admixed prior to admixing the base.

15. The method of claim 12, wherein the Lewis acid comprises stannous triflate, stannic chloride, dialkylboron triflate, or titanium tetrachloride.

16. The method of claim 12, wherein the second base comprises $NaHCO_3$ or a phosphate.

* * * * *